(12) United States Patent
Lee et al.

(10) Patent No.: US 6,517,835 B2
(45) Date of Patent: Feb. 11, 2003

(54) GROWTH DIFFERENTIATION FACTOR-11

(75) Inventors: Se-Jin Lee, Baltimore, MD (US); Alexandra C. McPherron, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/454,540

(22) Filed: Dec. 6, 1999

(65) Prior Publication Data

US 2001/0053358 A1 Dec. 20, 2001

Related U.S. Application Data

(62) Division of application No. 08/795,671, filed on Feb. 6, 1997, now Pat. No. 6,008,434, which is a continuation-in-part of application No. 08/706,958, filed on Sep. 3, 1996, which is a continuation of application No. 08/272,763, filed on Jul. 8, 1994, now abandoned.

(51) Int. Cl.[7] .................. A61K 39/395; C07K 16/00
(52) U.S. Cl. .................. 424/158.1; 424/130.1; 424/133.1; 424/139.1; 424/141.1; 424/145.1; 530/388.1; 530/389.1
(58) Field of Search ................ 424/130.1, 133.1, 424/139.1, 141.1, 145.1, 158.1; 530/388.1, 389.1

(56) References Cited

U.S. PATENT DOCUMENTS

| | | | |
|---|---|---|---|
| 5,585,479 A | 12/1996 | Hoke et al. ............. 536/24.5 |
| 5,639,638 A | 6/1997 | Wozney et al. | |
| 5,700,911 A | 12/1997 | Wozney et al. | |
| 6,004,937 A | 12/1999 | Wood et al. | |

FOREIGN PATENT DOCUMENTS

| | | |
|---|---|---|
| WO | WO9421681 | 9/1994 |
| WO | WO9426892 | 11/1994 |
| WO | WO9601845 | 1/1996 |
| WO | WO9833887 | 6/1998 |
| WO | WO9902667 | 1/1999 |

OTHER PUBLICATIONS

Evock et al., Journal of Animal Science, vol. 66, pp. 1928–1941, 1998.

Flakoll et al., Journal of Animal Science, vol. 69, pp. 1461–1467, 1991.

Gura, Science, vol. 270, pp. 575–577; Oct. 27, 1995.

Zhu et al., Poultry Science, vol. 74, pp. 1067–1073, 1995.

Faulkner et al., Journal of Animal Science, vol. 67, pp. 1907–1915, 1987.

McDowell et al., Australian Journal of Biological Sciences, vol. 40, pp. 295–306, 1987.

Kappel et al., Current Opinion in Biotechnology, vol. 3, pp. 548–553; 1992.

Strojek & Wagner, Genetic Engineering; Principles and Methods, vol. 10, pp. 221–246; 1988.

Ebert et al., Molecular Endocrinology, vol. 2, pp. 277–283; 1988.

Hammer et al., Journal of Animal Science, vol. 63, pp. 269–278; 1986.

Moreadith et al., Journal of Molecular Medicine, vol. 75, pp. 208–216; 1997.

Bradley et al., Biotechnology, vol. 10, pp. 534–539; 5/92.

Seamark, Reproduction, Fertility and Development, vol. 6, pp. 653–657; 1994.

Mullins et al., Journal of Clinical Investigation, vol. 98, pp. S37–S40; 1996.

Wall, Theriogenology, vol. 45, pp. 57–68; 1996.

Kulkarni et al., Proc. Nat. Acad. Sci. 90, 770–774, 1993.

Kaartinen et al., Nature Genetics 11, 415–421, 1995.

Foitzik et al., Developmental Biology 212, 278–289, 1999.

Massagué, Annu. Rev. Cell Biol. 1990, 6: 597–641.

Sampath et al.Proc. Natl., Acad. Sci., USA, vol. 90, pp. 6004–6008, Jul. 1993, Biochemistry.

*Primary Examiner*—Yvonne Eyler
*Assistant Examiner*—Janet L. Andres
(74) *Attorney, Agent, or Firm*—Gray Cary Ware & Friedenrich LLP; Lisa A. Haile; Richard J. Imbra

(57) ABSTRACT

A transgenic non-human animal of the species selected from the group consisting of avian, bovine, ovine and porcine having a transgene which results in disrupting the production of and/or activity of growth differentiation factor-11 (GDF-11) chromosomally integrated into the germ cells of the animal is disclosed. Also disclosed are methods for making such animals, and methods of treating animals with antibodies or antisense directed to GDF-11. The animals so treated are characterized by increased muscle tissue.

15 Claims, 14 Drawing Sheets

```
  1  TCTAGATGTCAAGAGAAGTGGTCACAATGTCTGGGTGGGAGCCGTAAACAAGCCAAGAGG   60
 61  TTATGGTTTCTGGTCTGATGCTCCTGTTGAGATCAGGAAATGTTCAGGAAATCCCCTGTT  120
121  GAGATGTAGGAAAGTAAGAGGTAAGAGACATTGTTGAGGGTCATGTCACATCTCTTTCCC  180
181  CTCTCCCTGACCCTCAGCATCCTTTCATGGAGCTTCGAGTCCTAGAGAACACGAAAAGGT  240
                   H  P  F  M  E  L  R  V  L  E  N  T  K   R  S
241  CCCGGCGGAACCTAGGCCTGGACTGCGATGAACACTCGAGTGAGTCCCGCTGCTGCCGAT  300
      R  R   N  L  G  L  D  C  D  E  H  S  S  E  S  R  C  C  R  Y
301  ATCCTCTCACAGTGGACTTTGAGGCTTTTGGCTGGGACTGGATCATCGCACCTAAGCGCT  360
      P  L  T  V  D  F  E  A  F  G  W  D  W  I  I  A  P  K  R  Y
361  ACAAGGCCAACTACTGCTCCGGCCAGTGCGAATACATGTTCATGCAAAAGTATCCACACA  420
      K  A  N  Y  C  S  G  Q  C  E  Y  M  F  M  Q  K  Y  P  H  T
421  CCCACTTGGTGCAACAGGCCAACCCAAGAGGCTCTGCTGGGCCCTGCTGCACCCCTACCA  480
      H  L  V  Q  Q  A  N  P  R  G  S  A  G  P  C  C  T  P  T  K
481  AGATGTCCCCAATCAACATGCTCTACTTCAATGACAAGCAGCAGATTATCTACGGCAAGA  540
      M  S  P  I  N  M  L  Y  F  N  D  K  Q  Q  I  I  Y  G  K  I
541  TCCCTGGCATGGTGGTGGATCGATGTGGCTGCTCCTAAGTTGTGGGCTACAGTGGATGCC  600
      P  G  M  V  V  D  R  C  G  C  S  *
601  TCCCTCAGACCCTACCCCAAGAACCCCAGC                              630
```

FIG. 1a

```
   1  CCGCGGGACTCCGGCGTCCCCGCCCCCCAGTCCTCCCTCCCCTCCCCTCCAGCATGGTGC    60
                                                              M  V  L
  61  TCGCGGCCCCGCTGCTGCTGGGCTTCCTGCTCCTCGCCCTGGAGCTGCGGCCCCGGGGG   120
       A  A  P  L  L  L  G  F  L  L  L  A  L  E  L  R  P  R  G  E
 121  AGGCGGCCGAGGGCCCCGCGGCGGCGGCGGCGGCGGCGGCGGCGGCAGCGGCGGGGG     180
       A  A  E  G  P  A  A  A  A  A  A  A  A  A  A  A  A  A  G  V
 181  TCGGGGGGGAGCGCTCCAGCCGGCCAGCCCCGTCCGTGGCGCCCGAGCCGGACGGCTGCC  240
       G  G  E  R  S  S  R  P  A  P  S  V  A  P  E  P  D  G  C  P
 241  CCGTGTGCGTTTGGCGGCAGCACAGCCGCGAGCTGCGCCTAGAGAGCATCAAGTCGCAGA  300
       V  C  V  W  R  Q  H  S  R  E  L  R  L  E  S  I  K  S  Q  I
 301  TCTTGAGCAAACTGCGGCTCAAGGAGGCGCCCAACATCAGCCGCGAGGTGGTGAAGCAGC  360
       L  S  K  L  R  L  K  E  A  P |N  I  S| R  E  V  V  K  Q  L
 361  TGCTGCCCAAGGCGCCGCCGCTGCAGCAGATCCTGGACCTACACGACTTCCAGGGCGACG  420
       L  P  K  A  P  P  L  Q  Q  I  L  D  L  H  D  F  Q  G  D  A
 421  CGCTGCAGCCCGAGGACTTCCTGGAGGAGGACGAGTACCACGCCACCACCGAGACCGTCA  480
       L  Q  P  E  D  F  L  E  E  D  E  Y  H  A  T  T  E  T  V  I
 481  TTAGCATGGCCCAGGAGACGGACCCAGCAGTACAGACAGATGGCAGCCCTCTCTGCTGCC  540
       S  M  A  Q  E  T  D  P  A  V  Q  T  D  G  S  P  L  C  C  H
 541  ATTTTCACTTCAGCCCCAAGGTGATGTTCACAAAGGTACTGAAGGCCCAGCTGTGGGTGT  600
       F  H  F  S  P  K  V  M  F  T  K  V  L  K  A  Q  L  W  V  Y
 601  ACCTACGGCCTGTACCCCGCCCAGCCACAGTCTACCTGCAGATCTTGCGACTAAAACCCC  660
       L  R  P  V  P  R  P  A  T  V  Y  L  Q  I  L  R  L  K  P  L
 661  TAACTGGGGAAGGGACCGCAGGGGGAGGGGGCGGAGGCCGGCGTCACATCCGTATCCGCT  720
       T  G  E  G  T  A  G  G  G  G  G  R  R  H  I  R  I  R  S
 721  CACTGAAGATTGAGCTGCACTCACGCTCAGGCCATTGGCAGAGCATCGACTTCAAGCAAG  780
       L  K  I  E  L  H  S  R  S  G  H  W  Q  S  I  D  F  K  Q  V
 781  TGCTACACAGCTGGTTCCGCCAGCCACAGAGCAACTGGGGCATCGAGATCAACGCCTTTG  840
       L  H  S  W  F  R  Q  P  Q  S  N  W  G  I  E  I  N  A  F  D
 841  ATCCCAGTGGCACAGACCTGGCTGTCACCTCCCTGGGCCGGGAGCCGGAGGGGCTGCATC  900
       P  S  G  T  D  L  A  V  T  S  L  G  P  G  A  E  G  L  H  P
 901  CATTCATGGAGCTTCGAGTCCTAGAGAACACAAAACGTTCCCGGCGGAACCTGGGTCTGG  960
       F  M  E  L  R  V  L  E  N  T  K |R  S  R  R| N  L  G  L  D
 961  ACTGCGACGAGCACTCAAGCGAGTCCCGCTGCTGCCGATATCCCCTCACAGTGGACTTTG 1020
       C  D  E  H  S  S  E  S  R  C  C  R  Y  P  L  T  V  D  F  E
1021  AGGCTTTCGGCTGGGACTGGATCATCGCACCTAAGCGCTACAAGGCCAACTACTGCTCCG 1080
       A  F  G  W  D  W  I  I  A  P  K  R  Y  K  A  N  Y  C  S  G
1081  GCCAGTGCGAGTACATGTTCATGCAAAAATATCCGCATACCCATTTGGTGCAGCAGGCCA 1140
       Q  C  E  Y  M  F  M  Q  K  Y  P  H  T  H  L  V  Q  Q  A  N
1141  ATCCAAGAGGCTCTGCTGGGCCCTGTTGTACCCCCACCAAGATGTCCCCAATCAACATGC 1200
       P  R  G  S  A  G  P  C  C  T  P  T  K  M  S  P  I  N  M  L
1201  TCTACTTCAATGACAAGCAGCAGATTATCTACGGCAAGATCCCTGGCATGGTGGTGGATC 1260
       Y  F  N  D  K  Q  Q  I  I  Y  G  K  I  P  G  M  V  V  D  R
1261  GCTGTGGCTGCTCTTAAGTGGGTCACTACAAGCTGCTGGAGCAAAGACTTGGTGGGTGGG 1320
       C  G  C  S  *
1321  TAACTTAACCTCTTCACAGAGGATAAAAAATGCTTGTGAGTATGACAGAAGGGAATAAAC 1380
1381  AGGCTTAAAGGGT  1393
```

```
  1 MVLAAPLLLGFLLLALELRPRGEAAEGPAAAAAAAAAAAAAAGVGGERSSR  50
    |                                          | |    |
  1 MQKLQLCVYIYLFML.......................IVAGPVDLNENSE  28

51 PAPSVAPEPDGCPVCVWRQHSRELRLESIKSQILSKLRLKEAPNISREVV 100
    |  |   |  |||        |  |  || |||||||||  |||||  |
 29 QKENVEKE.GLCNACTWRQNTKSSRIEAIKIQILSKLRLETAPNISKDVI  77

101 KQLLPKAPPLQQILDLHDFQGDALQPEDFLEEDEYHATTETVISMAQETD 150
    ||||||||||   |  |           ||  |||||||  | |  |  |
 78 RQLLPKAPPLRELIDQYDVQRDD.SSDGSLEDDDYHATTETIITMPTESD 126

151 PAVQTDGSPLCCHFHFSPKVMFTKVLKAQLWVYLRPVPRPATVYLQILRL 200
    |  || | || |  | |     |  || ||||| |||||   |  |||||
127 FLMQVDGKPKCCFFKFSSKIQYNKVVKAQLWIYLRPVETPTTVFVQILRL 176

201 KPLTGEGTAGGGGGGRRHIRIRSLKIELHSRSGHWQSIDFKQVLHSWFRQ 250
        ||             |     |||||     | |||||   | |  |
177 IKPMKDGT........RYTGIRSLKLDMNPGTGIWQSIDVKTVLQNWLKQ 218

251 PQSNWGIEINAFDPSGTDLAVTSLGPGAEGLHPFMELRVLENTKRSRRNL 300
    |  || ||||  |   |  ||||| |||||| | |  |  |    |||||
219 PESNLGIEIKALDENGHDLAVTFPGPGEDGLNPFLEVKVTDTPKRSRRDF 268

301 GLDDEHSSESRCCRYPLTVDFEAFGWDWIIAPKRYKANYCSGQCEYMFM 350
    ||||||||| |||||||||||||||||||||||||||||||||||||| |
269 GLDDEHSTESRCCRYPLTVDFEAFGWDWIIAPKRYKANYCSGECEFVFL 318

351 QKYPHTHLVQQANPRGSAGPCCTPTKMSPINMLYFNDKQQIIYGKIPGMV 400
    |||||||| |||||||||||||||||||||||||||| | |||||||| ||
319 QKYPHTHLVHQANPRGSAGPCCTPTKMSPINMLYFNGKEQIIYGKIPAMV 368

401 VDRCGCS 407
    |||||||
369 VDRCGCS 375
```

FIG. 4

```
  1  GTCTCTCGGACGGTACATGCACTAATATTTCACTTGGCATTACTCAAAAGCAAAAAGAAG   60
 61  AAATAAGAACAAGGGAAAAAAAAAGATTGTGCTGATTTTTAAAATGATGCAAAAACTGCA  120
                                              M M Q K L Q
121  AATGTATGTTTATATTTACCTGTTCATGCTGATTGCTGCTGGCCCAGTGGATCTAAATGA  180
      M Y V Y I Y L F M L I A A G P V D L N E
181  GGGCAGTGAGAGAGAAGAAAATGTGGAAAAAGAGGGGCTGTGTAATGCATGTGCCGTGGAG  240
      G S E R E E N V E K E G L C N A C A W R
241  ACAAAACACGAGGTACTCCAGAATAGAAGCCATAAAAATTCAAATCCTCAGTAAGCTGCG  300
      Q N T R Y S R I E A I K I Q I L S K L R
301  CCTGGAAACAGCTCCTAACATCAGCAAAGATGCTATAAGACAACTTCTGCCAAGAGCGCC  360
      L E T A P N I S K D A I R Q L L P R A P
361  TCCACTCCGGGAACTGATCGATCAGTACGACGTCCAGAGGGATGACAGCAGTGATGGCTC  420
      P L R E L I D Q Y D V Q R D D S S D G S
421  TTTGGAAGATGACGATTATCACGCTACCACGGAAACAATCATTACCATGCCTACAGAGTC  480
      L E D D D Y H A T T E T I I T M P T E S
481  TGACTTTCTAATGCAAGCGGATGGCAAGCCCAAATGTTGCTTTTTTAAATTTAGCTCTAA  540
      D F L M Q A D G K P K C C F F K F S S K
541  AATACAGTACAACAAAGTAGTAAAAGCCCAACTGTGGATATATCTCAGACCCGTCAAGAC  600
      I Q Y N K V V K A Q L W I Y L R P V K T
601  TCCTACAACAGTGTTTGTGCAAATCCTGAGACTCATCAAACCCATGAAAGACGGTACAAG  660
      P T T V F V Q I L R L I K P M K D G T R
661  GTATACTGGAATCCGATCTCTGAAACTTGACATGAGCCCAGGCACTGGTATTTGGCAGAG  720
      Y T G I R S L K L D M S P G T G I W Q S
721  TATTGATGTGAAGACAGTGTTGCAAAATTGGCTCAAACAGCCTGAATCCAACTTAGGCAT  780
      I D V K T V L Q N W L K Q P E S N L G I
781  TGAAATCAAAGCTTTGGATGAGAATGGCCATGATCTTGCTGTAACCTTCCCAGGACCAGG  840
      E I K A L D E N G H D L A V T F P G P G
841  AGAAGATGGGCTGAATCCCTTTTTAGAAGTCAAGGTGACAGACACACCCAAGAGGTCCCG  900
      E D G L N P F L E V K V T D T P K R S R
901  GAGAGACTTTGGGCTTGACTGCGATGAGCACTCCACGGAATCCCGGTGCTGCCGCTACCC  960
      R D F G L D C D E H S T E S R C C R Y P
961  CCTCACGGTCGATTTTGAAGCCTTTGGATGGGACTGGATTATCGCACCCAAAAGATATAA 1020
      L T V D F E A F G W D W I I A P K R Y K
1021 GGCCAATTACTGCTCAGGAGAGTGTGAATTTGTGTTTTTACAAAAATATCCGCATACTCA 1080
      A N Y C S G E C E F V F L Q K Y P H T H
1081 TCTTGTGCACCAAGCAAACCCCAGAGGCTCAGCAGGCCCTTGCTGCACTCCGACAAAAAT 1140
      L V H Q A N P R G S A G P C C T P T K M
1141 GTCTCCCATTAATATGCTATATTTTAATGGCAAAGAACAAATAATATATGGGAAAATTCC 1200
      S P I N M L Y F N G K E Q I I Y G K I P
1201 AGCCATGGTAGTAGACCGCTGTGGGTGCTCATGAGCTTTGCATTAGGTTAGAAACTTCCC 1260
      A M V V D R C G C S *
```

FIG. 8a

```
1261 AAGTCATGGAAGGTCTTCCCCTCAATTTCGAAACTGTGAATTCAAGCACCACAGGCTGTA 1320
1321 GGCCTTGAGTATGCTCTAGTAACGTAAGCACAAGCTACAGTGTATGAACTAAAAGAGAGA 1380
1381 ATAGATGCAATGGTTGGCATTCAACCACCAAAATAAACCATACTATAGGATGTTGTATGA 1440
1441 TTTCCAGAGTTTTTGAAATAGATGGAGATCAAATTACATTTATGTCCATATATGTATATT 1500
1501 ACAACTACAATCTAGGCAAGGAAGTGAGAGCACATCTTGTGGTCTGCTGAGTTAGGAGGG 1560
1561 TATGATTAAAAGGTAAAGTCTTATTTCCTAACAGTTTCACTTAATATTTACAGAAGAATC 1620
1621 TATATGTAGCCTTTGTAAAGTGTAGGATTGTTATCATTTAAAAACATCATGTACACTTAT 1680
1681 ATTTGTATTGTATACTTGGTAAGATAAAATTCCACAAAGTAGGAATGGGGCCTCACATAC 1740
1741 ACATTGCCATTCCTATTATAATTGGACAATCCACCACGGTGCTAATGCAGTGCTGAATGG 1800
1801 CTCCTACTGGACCTCTCGATAGAACACTCTACAAAGTACGAGTCTCTCTCTCCCTTCCAG 1860
1861 GTGCATCTCCACACACACAGCACTAAGTGTTCAATGCATTTTCTTTAAGGAAAGAAGAAT 1920
1921 CTTTTTTTCTAGAGGTCAACTTTCAGTCAACTCTAGCACAGCGGGAGTGACTGCTGCATC 1980
1981 TTAAAAGGCAGCCAAACAGTATTCATTTTTTAATCTAAATTTCAAAATCACTGTCTGCCT 2040
2041 TTATCACATGGCAATTTTGTGGTAAAATAATGGAAATGACTGGTTCTATCAATATTGTAT 2100
2101 AAAAGACTCTGAAACAATTACATTTATATAATATGTATACAATATTGTTTTGTAAATAAG 2160
2161 TGTCTCCTTTTATATTTACTTTGGTATATTTTTACACTAATGAAATTTCAAATCATTAAA 2220
2221 GTACAAAGACATGTCATGTATCACAAAAAAGGTGACTGCTTCTATTTCAGAGTGAATTAG 2280
2281 CAGATTCAATAGTGGTCTTAAAACTCTGTATGTTAAGATTAGAAGGTTATATTACAATCA 2340
2341 ATTTATGTATTTTTTACATTATCAACTTATGGTTTCATGGTGGCTGTATCTATGAATGTG 2400
2401 GCTCCCAGTCAAATTTCAATGCCCCACCATTTTAAAAATTACAAGCATTACTAAACATAC 2460
2461 CAACATGTATCTAAAGAAATACAAATATGGTATCTCAATAACAGCTACTTTTTTATTTTA 2520
2521 TAATTTGACAATGAATACATTTCTTTTATTTACTTCAGTTTTATAAATTGGAACTTTGTT 2580
2581 TATCAAATGTATTGTACTCATAGCTAAATGAAATTATTTCTTACATAAAAATGTGTAGAA 2640
2641 ACTATAAATTAAAGTGTTTTCACATTTTTGAAAGCC 2676
```

FIG. 8b

GROWTH DIFFERENTIATION FACTOR-11

This application is a divisional of U.S. application Ser. No. 08/795,671, filed on Feb. 6, 1997, now U.S. Pat. No. 6,008,434; which is a continuation-in-part of prior U.S. application Ser. No. 08/706,958, filed Sep. 3, 1996, now pending; which is a continuation of prior U.S. application Ser. No. 08/272,763, filed Jul. 8, 1994, now abandoned; the entire contents of which are hereby incorporated by reference herein.

BACKGROUND OF THE INVENTION

1. Field of the Invention

The invention relates generally to growth factors and specifically to a new member of the transforming growth factor beta (TGF-β) superfamily, which is denoted, growth differentiation factor-11 (GDF-11).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., Nature, 345:167, 1990), Drosophila decapentaplegic (DPP) gene product, which is required for dorsal-ventral axis formation and morphogenesis of the imaginal disks (Padgett, et al., Nature, 325:81–84, 1987), the Xenopus Vg-1 gene product, which localizes to the vegetal pole of eggs ((Weeks, et al., Cell, 51:861–867, 1987), the activins (Mason, et al., Biochem, Biophys. Res. Commun., 135:957–964, 1986), which can induce the formation of mesoderm and anterior structures in Xenopus embryos (Thomsen, et al., Cell, 63:485, 1990), and the bone morphogenetic proteins (BMPs, osteogenin, OP-1) which can induce de novo cartilage and bone 5 formation (Sampath, et al., J. Biol. Chem., 265:13198, 1990). The TGF βs can influence a variety of differentiation processes, including adipogenesis, myogenesis, chondrogenesis, hematopolesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A. et al., Science, 247:1328, 1990). Additional studies by Hammonds, et al., (Molec. Endocrin. 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., Nature, 321:779, 1986) and the TGF-βs (Cheifetz, et al., Cell, 48:409, 1987), heterodimers have also been detected,. and these appear to have different biological properties than the respective homodimers.

In addition it is desirable to produce livestock and game animals, such as cows, sheep, pigs, chicken and turkey, fish which are relatively high in musculature and protein, and low in fat content. Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to produce animals which are genetically predisposed to having higher muscle content, without any ancillary increase in fat levels.

The food industry has put much effort into increasing the amount of muscle and protein in foodstuffs. This quest is relatively simple in the manufacture of synthetic foodstuffs, but has been met with limited success in the preparation of animal foodstuffs. Attempts have been made, for example, to lower cholesterol levels in beef and poultry products by including cholesterol-lowering drugs in animal feed (see e.g. Elkin and Rogler, J. Agric. Food Chem. 1990, 38, 1635–1641). However, there remains a need for more effective methods of increasing muscle and reducing fat and cholesterol levels in animal food products.

SUMMARY OF THE INVENTION

The present invention provides a cell growth and differentiation factor, GDF-11, a polynucleotide sequence which encodes the factor, and antibodies which are immunoreactive with the factor. This factor appears to relate to various cell proliferative disorders, especially those involving muscle, nerve, and adipose tissue.

In one embodiment, the invention provides a method for detecting a cell proliferative disorder of muscle, nerve, or fat origin and which is associated with GDF-11. In another embodiment, the invention provides a method for treating a cell proliferative disorder by suppressing or enhancing GDF-11 activity.

In another embodiment, the subject invention provides non-human transgenic animals which are useful as a source of food products with high muscle and protein content, and reduced fat and cholesterol content. The animals have been altered chromosomally in their germ cells and somatic cells so that the production of GDF-11 is produced in reduced amounts, or is completely disrupted, resulting in animals with decreased levels of GDF-11 in their system and higher than normal levels of muscle tissue, preferably without increased fat and/or cholesterol levels. Accordingly, the present invention also includes food products provided by the animals. Such food products have increased nutritional value because of the increase in muscle tissue. The transgenic non-human animals of the invention include bovine, porcine, ovine and avian animals, for example.

The subject invention also provides a method of producing animal food products having increased muscle content. The method includes modifying the genetic makeup of the germ cells of a pronuclear embryo of the animal, implanting the embryo into the oviduct of a pseudopregnant female thereby allowing the embryo to mature to full term progeny, testing the progeny for presence of the transgene to identify transgene-positive progeny, cross-breeding transgene-positive progeny to obtain further transgene-positive progeny and processing the progeny to obtain foodstuff. The modification of the germ cell comprises altering the genetic composition so as to disrupt or reduce the expression of the naturally occurring gene encoding for production of GDF-11 protein. In a particular embodiment, the transgene comprises antisense polynucleotide sequences to the GDF-11 protein. Alternatively, the transgene may comprise a non-functional sequence which replaces or intervenes in the native GDF-11 gene.

The subject invention also provides a method of producing avian food products having improved muscle content. The method includes modifying the genetic makeup of the germ cells of a pronuclear embryo of the avian animal, implanting the embryo into the oviduct of a pseudopregnant female into an embryo of a chicken, culturing the embryo under conditions whereby progeny are hatched, testing the progeny for presence of the genetic alteration to identify transgene-positive progeny, cross-breeding transgene-positive progeny and processing the progeny to obtain foodstuff.

BRIEF DESCRIPTION OF THE DRAWINGS

FIG. 1 shows the nucleotide and predicted amino acid sequences of murine (FIG. 1a) and human (FIG. 1b) GDF-11. The putative proteolytic processing sites are shown by the shaded boxes. In the human sequence, the potential N-linked glycosylation signal is shown by the open box, and the consensus polyadenylation signal is underlined; the poly A tail is not shown.

FIG. 3 shows amino acid homologies among different members of the TGF-β superfamily. Numbers represent percent amino acid identities between each pair calculated from the first conserved cysteine to the C-terminus. Boxes represent homologies among highly-related members within particular subgroups.

FIG. 4 shows an alignment of the predicted amino acid sequences of human GDF-11 (top lines) with human GDF-8 (bottom lines). Vertical lines indicate identities. Dots represent gaps introduced in order to maximize the alignment. Numbers represent amino acid positions relative to the N-terminus. The putative proteolytic processing sites are shown by the open box. The conserved cysteine residues on the C-terminal region are shown by the shaded boxes.

FIG. 8 shows the nucleotide and deduced amino acid sequence of murine GDF-8.

DETAILED DESCRIPTION OF THE INVENTION

Figure 2A:
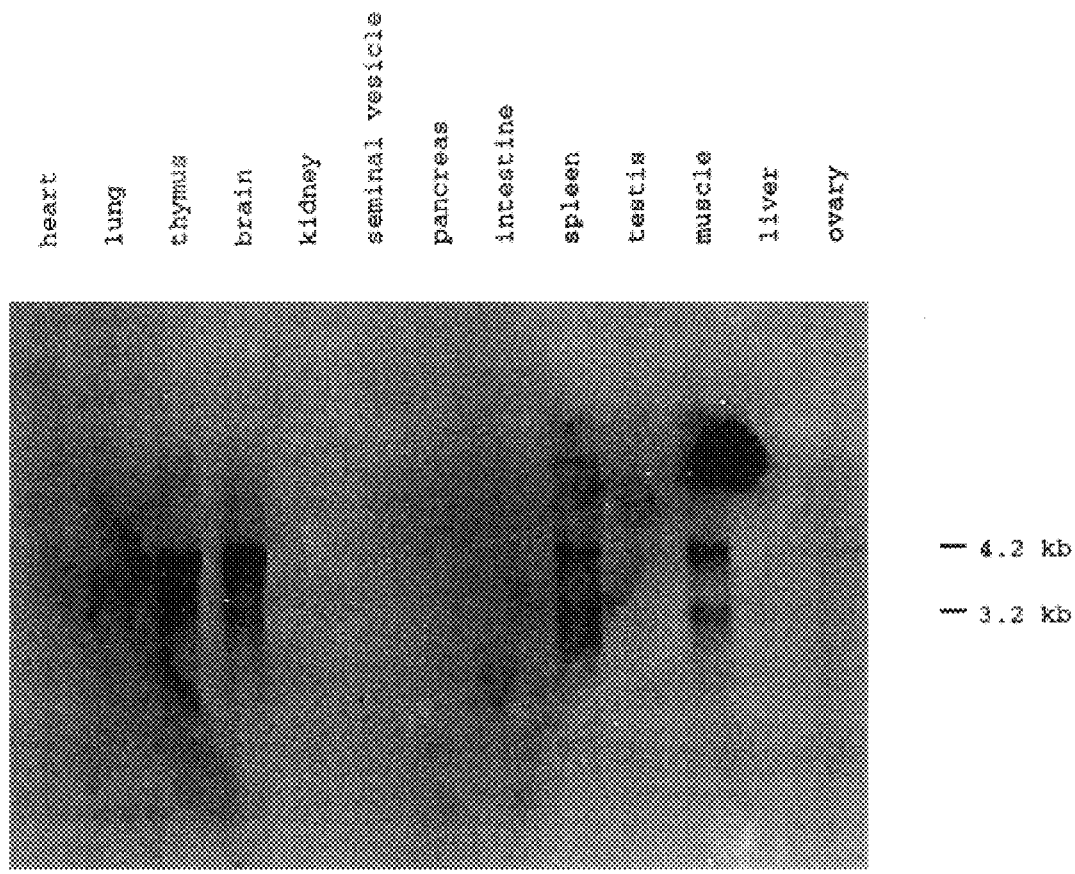
FIG. 2 shows Northern blots of RNA prepared from adult (FIG. 2a) or fetal and neonatal (FIG. 2b) tissues probed with a murine GDF-11 probe.

The present invention provides a growth and differentiation factor, GDF-11, and a polynucleotide sequence encoding GDF-11. GDF-11 is expressed at highest levels in muscle, brain, uterus, spleen, and thymus and at lower levels in other tissues.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-11 protein of this invention and the members of the TGF-β family, indicates that GDF-11 is a new member of the family of growth and differentiation factors. Based on the known activities of many of the other members, it can be expected that GDF-11 will also possess biological activities that will make it useful as a diagnostic and therapeutic reagent.

Certain members of this superfamily have expression patterns or possess activities that relate to the function of the nervous system. For example, one family member, namely GDNF, has been shown to be a potent neurotrophic factor that can promote the survival of dopaminergic neurons (Lin, et al., Science, 260:1130). Another family member, namely dorsalin-1, is capable of promoting the differentiation of neural crest cells (Basler, et al., Cell, 73:687, 1993). The inhibins and activins have been shown to be expressed in the brain (Meunier, et al., Proc. Nat'l. Acad. Sci., USA, 85:247, 1988; Sawchenko, et al., Nature., 334:615, 1988), and activin has been shown to be capable of functioning as a nerve cell survival molecule (Schubert, et al., Nature, 344:868, 1990). Another family member, namely GDF-1, is nervous system-specific in its expression pattern (Lee, Proc. Nat'l. Acad. Sci., USA, 88:4250, 1991), and certain other family members, such as Vgr-1 (Lyons, et al., Proc. Nat'l. Acad. Sci., USA, 86:4554, 1989; Jones, et al., Development, 111:581, 1991), OP-1 (Ozkaynak, et al., J. Biol. Chem., 267:25220, 1992), and BMP-4 (Jones, et al., Development, 111:531, 1991), are also known to be expressed in the nervous system. The expression of GDF-11 in brain and muscle suggests that GDF-11 may also possess activities that relate to the function of the nervous system. In particular, it is known, for example, that skeletal muscle produces a factor or factors that promote the survival of motor neurons (Brown, Trends Neurosci., 7:10, 1984). The known neurotrophic activities of other members of this family and the expression of GDF-11 in muscle suggest that one activity of GDF-11 may be as a trophic factor for motor neurons; indeed, GDF-11 is highly related to GDF-8, which is virtually muscle-specific in its expression pattern. Alternatively, GDF-11 may have neurotrophic activities for other neuronal populations. Hence, GDF-11 may have in vitro and in vivo applications in the treatment of neurodegenerative diseases, such as amyotrophic lateral sclerosis, or in maintaining cells or tissues in culture prior to transplantation.

GDF-11 may also have applications in treating disease processes involving muscle, such as in musculodegenerative diseases or in tissue repair due to trauma. In this regard, many other members of the TGF-β family are also important mediators of tissue repair.

TGF-β has been shown to have marked effects on the formation of collagen and to cause a striking angiogenic response in the newborn mouse (Roberts, et al., Proc. Natl. Acad. Sci., USA 83:4167, 1986). TGF-β has also been shown to inhibit the differentiation of myoblasts in culture (Massague, et al., Proc. Natl. Acad. Sci., USA 83:8206, 1986). Moreover, because myoblast cells may be used as a vehicle for delivering genes to muscle for gene therapy, the properties of GDF-11 could be exploited for maintaining cells prior to transplantation or for enhancing the efficiency of the fusion process.

GDF-11 may also have applications in the treatment of immunologic disorders. In particular, TGF-β has been shown to have a wide range of immunoregulatory activities, including potent suppressive effects on B and T cell proliferation and function (for review, see Palladino, et al., Ann. N.Y. Acad. Sci., 593:181, 1990). The expression of GDF-11 in spleen and thymus suggests that GDF-11 may possess similar activities and therefore, may be used as an anti-inflammatory agent or as a treatment for disorders related to abnormal proliferation or function of lymphocytes.

The animals contemplated for use in the practice of the subject invention are those animals generally regarded as useful for the processing of food stuffs, i.e. avian such as meat bred and egg laying chicken and turkey, ovine such as lamb, bovine such as beef cattle and milk cows, piscine and porcine. For purposes of the 25 subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-11 protein of this invention and the members of the TGF-β family, indicates that GDF-11 is a new member of the family of growth and differentiation factors. Based on the known activities of many of the other members, it can be expected that GDF-11 will also possess biological activities that will make it useful as a diagnostic and therapeutic reagent.

In particular, certain members of this superfamily have expression patterns or possess activities that relate to the function of the nervous system. For example, the inhibins and activins have been shown to be expressed in the brain (Meunier, et al., Proc. Natl. Acad. Sci., USA, 85:247, 1988; Sawchenko, et al., Nature, 334:615, 1988), and activin has been shown to be capable of functioning as a nerve cell survival molecule (Schubert, et al., Nature, 344:868, 1990). Another family member, namely, GDF-1, is nervous system-specific in its expression pattern (Lee, S. J., Proc. Natl. Acad. Sci., USA, 88:4250, 1991), and certain other family members, such as Vgr-1 (Lyons, et al., Proc. Natl. Acad. Sci., USA, 86:4554, 1989; Jones, et al., Development, 111:531, 1991), OP-1 (Ozkaynak, et al., J. Biol. Chem., 267:25220, 1992), and BMP-4 (Jones, et al., Development, 111:531, 1991), are also known to be expressed in the nervous system. Because it is known that skeletal muscle produces a factor or factors that promote the survival of motor neurons (Brown, Trends Neurosci., 7:10, 1984), the expression of GDF-11 in muscle suggests that one activity of GDF-11 may be as a trophic factor for neurons. In this regard, GDF-11 may have applications in the treatment of neurodegenerative diseases, such as amyotrophic lateral sclerosis or muscular dystrophy, or in maintaining cells or tissues in culture prior to transplantation.

GDF-11 may also have applications in treating disease processes involving muscle, such as in musculodegenerative diseases or in tissue repair due to trauma. In this regard, many other members of the TGF-β family are also important mediators of tissue repair. TGF-β has been shown to have marked effects on the formation of collagen and to cause a striking angiogenic response in the newborn mouse (Roberts, et al., Proc. Natl. Acad. Sci., USA 83:4167, 1986). TGF-β has also been shown to inhibit the differentiation of myoblasts in culture (Massague, et al., Proc. Natl. Acad. Sci., USA 83:8206, 1986). Moreover, because myoblast cells may be used as a vehicle for delivering genes to muscle for gene therapy, the properties of GDF-11 could be exploited for maintaining cells prior to transplantation or for enhancing the efficiency of the fusion The expression of GDF-11 in adipose tissue also raises the possibility of applications for GDF-11 in the treatment of obesity or of disorders related to abnormal proliferation of adipocytes. In this regard, TGF-β has been shown to be a potent inhibitor of adipocyte differentiation in vitro (Ignotz and Massague, Proc. Natl. Acad. Sci., USA 82:8530, 1985).

The term "substantially pure" as used herein refers to GDF-11 which is substantially free of other proteins, lipids, carbohydrates or other materials with which it is naturally associated. One skilled in the art can purify GDF-11 using standard techniques for protein purification. The substantially pure polypeptide will yield a single major band on a non-reducing polyacrylamide gel. The purity of the GDF-11 polypeptide can also be determined by amino-terminal amino acid sequence analysis. GDF-11 polypeptide includes functional fragments of the polypeptide, as long as the activity of GDF-11 remains. Smaller peptides containing the biological activity of GDF-11 are included in the invention.

The invention provides polynucleotides encoding the GDF-11 protein. These polynucleotides include DNA, cDNA and RNA sequences which encode GDF-11. It is understood that all polynucleotides encoding all or a portion of GDF-11 are also included herein, as long as they encode a polypeptide with GDF-11 activity. Such polynucleotides include naturally occurring, synthetic, and intentionally manipulated polynucleotides. For example, GDF-11 polynucleotide may be subjected to site-directed mutagenesis. The polynucleotide sequence for GDF11 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-11 polypeptide encoded by the nucleotide sequence is functionally unchanged.

Specifically disclosed herein is a DNA sequence containing the human GDF-11 gene. The sequence contains an open reading frame encoding a polypeptide 407 amino acids in length. The sequence contains a putative RXXR proteolytic cleavage site at amino acids 295–298. Cleavage of the precursor at this site would generate an active C-terminal fragment 109 amino acids in length with a predicted molecular weight of approximately 12,500 kD. Also disclosed herein is a partial murine genomic sequence. Preferably, the human GDF-11 nucleotide sequence is SEQ ID NO:1 and the mouse nucleotide sequence is SEQ ID NO:3.

The polynucleotide encoding GDF-11 includes SEQ ID NO:1 and 3, as well as nucleic acid sequences complementary to SEQ ID NO's:1 and 3. A complementary sequence may include an antisense nucleotide. When the sequence is RNA, the deoxynucleotides A, G, C, and T of SEQ ID NO:1 and 3 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO: 2 or 4 under physiological conditions (e.g., under stringent conditions).

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The C-terminal region of GDF-11 following the putative proteolytic processing site shows significant homology to the known members of the TGF-β superfamily. The GDF-11 sequence contains most of the residues that are highly conserved in other family members (see FIG. 1). Like the TGF-βs and inhibin βs, GDF-11 contains an extra pair of cysteine residues in addition to the 7 cysteines found in virtually all other family members. Among the known family members, GDF-11 is most homologous to GDF-8 (92% sequence identity) (see FIG. 3).

Minor modifications of the recombinant GDF-11 primary amino acid sequence may result in proteins which have substantially equivalent activity as compared to the GDF-11 polypeptide described herein. Such modifications may be deliberate, as by site-directed mutagenesis, or may be spontaneous. All of the polypeptides produced by these modifications are included herein as long as the biological activity of GDF-11 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-11 biological activity.

The nucleotide sequence encoding the GDF-11 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features. Preferably the GDF-11 polynucleotide of the invention is derived from a mammalian organism, and most preferably from mouse, rat, cow, pig, or human. GDF-11 polynucleotides from chicken, fish and other species are also included herein. Screening procedures which rely on nucleic acid hybridization make it possible to isolate any gene sequence from any organism, provided the appropriate probe is available. oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

The development of specific DNA sequences encoding GDF-11 can also be obtained by: 1) isolation of double-stranded DNA sequences from the genomic DNA; 2) chemical manufacture of a DNA sequence to provide the necessary codons for the polypeptide of interest; and 3) in vitro synthesis of a doublestranded DNA sequence by reverse transcription of MRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of MRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A CDNA expression library, such as lambda gt11, can be screened indirectly for GDF-11 peptides having at least one epitope, using antibodies specific for GDF-11. Such antibodies can be either polyclonally or monoclonally derived and used to detect expression product indicative of the presence of GDF-11 cDNA.

DNA sequences encoding GDF-11 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-11 polynucleotide sequences may be inserted into a recombinant expression vector. The term "recombinant expression vector" refers to a plasmid, virus or other vehicle known in the art that has been manipulated by insertion or incorporation of the GDF-11 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 19117), the PMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding GDF-11 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-11 is expressed from a cDNA clone containing the entire coding sequence of GDF-11. Alternatively, the C-terminal portion of GDF-11 can be expressed as a fusion protein with the pro- region of another member of the TGF-β family or co-expressed with another pro-region (see for example, Hammonds, et al., *Molec. Endocrin.*, 5:149, 1991; Gray, A., and Mason, A., *Science*, 247:1328, 1990).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-11 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-11 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and $F(ab')_2$ Fv and SCA fragments which are capable of binding an epitopic determinant on GDF-11.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a GDF-11 polypeptide, to which the paratope of an antibody, such as an GDF-11-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing GDF-11-specific antibodies include GDF-11 polypeptides or GDF-11 polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-11 polynucleotide that is an antisense molecule is useful in treating malignancies of the various organ systems, particularly, for example, cells in muscle or adipose tissue. Essentially, any disorder which is etiologically linked to altered expression of GDF-11 could be considered susceptible to treatment with a GDF-11 agent (e.g., a suppressing or enhancing agent). One such disorder is a malignant cell proliferative disorder, for example.

The invention provides a method for detecting a cell proliferative disorder of muscle, uterine or neural tissue, for example, which comprises contacting an anti-GDF-11 antibody with a cell suspected of having a GDF-11 associated disorder and detecting binding to the antibody. The antibody reactive with GDF-11 is labeled with a compound which allows detection of binding to GDF-11. For purposes of the invention, an antibody specific for GDF-11 polypeptide may be used to detect the level of GDF-11 in biological fluids and tissues. Any specimen containing a detectable amount of antigen can be used. A preferred sample of this invention is muscle, uterus, spleen, thymus, or neural tissue. The level of GDF-11 in the suspect cell can be compared with the level in a normal cell to determine whether the subject has a GDF-11-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyi, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group, intermediate functional groups which often are used to bind radioisotopes which exist as metallic ions to immunoglobulins are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-11-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-11-associated disease is effective. The term "ameliorate" denotes a lessening of the detrimental effect of the GDF-11-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Treatment includes administration of a reagent which modulates activity. The term "modulate" envisions the suppression or expression of GDF-11 when it is over-expressed, or augmentation of GDF-11 expression when it is underexpressed. When a muscle-associated disorder is associated with GDF-11 overexpression, such suppressive reagents as antisense GDF-11 polynucleotide sequence or GDF-11 binding antibody can be introduced into a cell. In addition, an anti-idiotype antibody which binds to a monoclonal antibody which binds GDF-11 of the invention, or an epitope thereof, may also be used in the therapeutic method of the invention. Alternatively, when a cell proliferative disorder is associated with underexpression or expression of a mutant GDF-11 polypeptide, a sense polynucleotide sequence (the DNA coding strand) or GDF-11 polypeptide can be introduced into the cell. Such muscle-associated disorders include cancer, muscular dystrophy, spinal cord injury, traumatic injury, congestive obstructive pulmonary disease (COPD), AIDS or cachecia. Neurodegenerative disorders are also envisioned as treated by the method of the invention.

Thus, where a cell-proliferative disorder is associated with the expression of GDF-11, nucleic acid sequences that interfere with GDF-11 expression at the translational level can be used. This approach utilizes, for example, antisense nucleic acid and ribozymes to block translation of a specific GDF-11 mRNA, either by masking that mRNA with an antisense nucleic acid or by cleaving it with a ribozyme. Such disorders include neurodegenerative diseases, for example. In addition, dominant-negative GDF-11 mutants would be useful to actively interfere with function of "normal" GDF-11.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the MRNA, since the cell will not translate a mRNA that is double-stranded.

Antisense oligomers of about 15 nucleotides are preferred, since they are easily synthesized and are less likely to cause problems than larger molecules when introduced into the target GDF-11-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target MRNA species. Consequently, hammer-head-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-11 protein. Such therapy would achieve its therapeutic effect by introduction of the GDF-11 antisense polynucleotide into cells having the proliferative disorder. Delivery of antisense GDF-11 polynucleotide can be achieved using a recombinant expression vector such as a chimeric virus or a colloidal dispersion system. Especially preferred for therapeutic delivery of antisense sequences is the use of targeted liposomes. In contrast, when it is desirable to enhance GDF-11 production, a "sense" GDF-11 polynucleotide is introduced into the appropriate cell(s).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-11 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-11 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include, but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-11 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 19111). In addition to mammalian cells, liposomes have been used for delivery of polynucleotides in plant, yeast and bacterial cells. in order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyiglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-11 in muscle and adipose tissue, there are a variety of applications using the polypeptide, polynucleotide, and antibodies of the invention, related to these tissues. Such applications include treatment of cell proliferative disorders involving these and other tissues, such as neural tissue. In addition, GDF-11 may be useful in various gene therapy procedures. In embodiments where GDF-11 polypeptide is administered to a subject, the dosage range is about 0.1 ug/kg to 100 mg/kg; more preferably from about 1 ug/kg to 75 mg/kg and most preferably from about 10 mg/kg to 50 mg/kg.

The data in Example 6 shows that the human GDF-11 gene is located on chromosome 2. By comparing the chromosomal location of GDF-11 with the map positions of various human disorders, it should be possible to determine whether mutations in the GDF-11 gene are involved in the etiology of human diseases. For example, an autosomal recessive form of juvenile amyotrophic lateral sclerosis has been shown to map to chromosome 2 (Hentati, et al., *Neurology*, 42 [Suppl.3]:201, 1992). More precise mapping of GDF-11 and analysis of DNA from these patients may indicate that GDF-11 is, in fact, the gene affected in this disease. In addition, GDF-11 is useful for distinguishing chromosome 2 from other chromosomes.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is 11 the best target for micro-injection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258, 1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988). "Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode GDF-11, and include GDF-sense and antisense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a modified GDF-11 coding sequence. In a preferred embodiment, the GDF-11 gene is disrupted by homologous targeting in embryonic stem cells. For example, the entire mature C-terminal region of the GDF-11 gene may be deleted as described in the examples below. Optionally, the GDF-11 disruption or deletion may be accompanied by insertion of or replacement with other DNA sequences, such as a non-functional GDF-11 sequence. In other embodiments, the transgene comprises DNA antisense to the coding sequence for GDF-11. In another embodiment, the transgene comprises DNA encoding an antibody or receptor peptide sequence which is able to bind to GDF-11. The DNA and peptide sequences of GDF-11 are known in the art, the sequences, localization and activity disclosed in WO95/08543 and pending U.S. patent application Ser. No. 08/706,958, filed on Sep. 3, 1996, incorporated by reference in its entirety. The disclosure of both of these applications are hereby incorporated herein by reference. Where appropriate, DNA sequences that encode proteins having GDF-11 activity but differ in nucleic acid sequence due to the degeneracy of the genetic code may also be used herein, as may truncated forms, allelic variants and interspecies homologues.

Therefore the invention also includes animals having heterozygous mutations in GDF-11. A heterozygote would likely have an intermediate increase in muscle mass as compared to the homozygote.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous GDF-11 gene(s), a marker gene fragment can be included in the construct in the 3' untranslated region of the transgene and the Northern probe designed to probe for the marker gene fragment. The serum levels of GDF-11 can also be measured in the transgenic animal to establish appropriate expression. Expression of the GDF-11 transgenes, thereby decreasing the GDF-11 in the tissue and serum levels of the transgenic animals and consequently increasing the muscle tissue content results in the foodstuffs from these animals (i.e. eggs, beef, pork, poultry meat, milk, etc.) having markedly increased muscle content, and preferably without increased, and more preferably, reduced levels of fat and cholesterol. By practice of the subject invention, a statistically significant increase in muscle content, preferably at least a 2% increase in muscle content (e.g., in chickens), more preferably a 25% increase in muscle content as a percentage of body weight, more preferably greater than 40% increase in muscle content in these foodstuffs can be obtained.

Thus, the present invention includes methods for increasing muscle mass in domesticated animals, characterized by inactivation or deletion of the gene encoding growth and differentiation factor-11 (GDF-11). The domesticated animal is preferably selected from the group consisting of ovine, bovine, porcine, piscine and avian. The animal may be treated with an isolated polynucleotide sequence encoding growth and differentiation factor-11 which polynucleotide sequence is also from a domesticated animal selected from the group consisting of ovine, bovine, porcine, piscine and avian. The present invention includes methods for increasing the muscle mass in domesticated animals characterized by administering to a domesticated animal monoclonal antibodies directed to the GDF-11 polypeptide. The antibody may be an anti-GDF-11, and may be either a monoclonal antibody or a polyclonal antibody.

The invention includes methods comprising using an anti-GDF-11 monoclonal antibody as a therapeutic agent to inhibit the growth regulating actions of GDF-11 on muscle cells. Muscle cells are defined to include fetal or adult muscle cells, as well as progenitor cells which are capable of differentiation into muscle. The monoclonal antibody may be a humanized (e.g., either fully or a chimeric) monoclonal antibody, of any species origin, such as murine, ovine, bovine, porcine or avian. Methods of producing antibody molecules with various combinations of "humanized" antibodies are well known in the art and include combining murine variable regions with human constant regions (Cabily, et al. *Proc. Natl. Acad. Sci. USA*, 81:3273, 1984), or by grafting the murine-antibody complementary determining regions (CDRs) onto the human framework (Richmann, et al., *Nature* 332:323, 1988). Other general references which teach methods for creating humanized antibodies include Morrison, et al., *Science*, 229:1202, 1985; Jones, et al., *Nature*, 321:522, 1986; Monroe, et al., *Nature 312:779, 1985*; Oi, et al., *BioTechniques*, 4:214, 1986; European Patent Application No. 302,620; and U.S. Pat. No. 5,024,834. Therefore, by humanizing the monoclonal antibodies of the invention for in vivo use, an immune response to the antibodies would be greatly reduced.

The monoclonal antibody, GDF-11 polypeptide, or GDF-11 polynucleotide (all "GDF-11 agents") may have the effect of increasing the development of skeletal muscles. In preferred embodiments of the claimed methods, the GDF-11 monoclonal antibody, polypeptide, or polynucleotide is administered to a patient suffering from a disorder selected from the group consisting of muscle wasting disease, neuromuscular disorder, muscle atrophy or aging. The GDF-11 agent may also be administered to a patient suffering from a disorder selected from the group consisting of muscular dystrophy, spinal cord injury, traumatic injury, congestive obstructive pulmonary disease (COPD), AIDS or cachechia. In a preferred embodiment, the GDF-11 agent is administered to a patient with muscle wasting disease or disorder by intravenous, intramuscular or subcutaneous injection; preferably, a monoclonal antibody is administered within a dose range between about 0.1 mg/kg to about 100 mg/kg; more preferably between about 1 ug/kg to 75 mg/kg; most preferably from about 10 mg/kg to 50 mg/kg. The antibody may be administered, for example, by bolus injunction or by slow infusion. Slow infusion over a period of 30 minutes to 2 hours is preferred. The GDF-11 agent may be formulated in a formulation suitable for administration to a patient. Such formulations are known in the art.

The dosage regimen will be determined by the attending physician considering various factors which modify the action of the GDF-11 protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of agent, such as anti-GDF-11 antibodies, to be used in the composition. Generally, systemic or injectable administration, such as intravenous (IV), intramuscular (IM) or subcutaneous (Sub-Q) injection. Administration will generally be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), human, bovine, or chicken growth hormone which may aid in increasing muscle mass, to the final composition, may also affect the dosage. In the embodiment where an anti-GDF-11 antibody is administered, the anti-GDF-11 antibody is generally administered within a dose range of about 0.1 ug/kg to about 100 mg/kg.; more preferably between about 10 mg/kg to 50 mg/kg.

Progress can be monitored by periodic assessment of tissue growth and/or repair. The progress can be monitored, for example, x-rays, histomorphometric determinations and tetracycline labeling.

All references cited herein are hereby incorporated by reference in their entirety.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify novel members of the TGF-β superfamily, a murine genomic library was screened at reduced stringency using a murine GDF-8 probe (FIG. 8; nucleotides 865–1234) spanning the region encoding the C-terminal portion of the GDF-8 precursor protein. Hybridization was carried out as described (Lee, Mol. Endocrinol., 4:1034, 1990) at 65° C., and the final wash was carried out at the same temperature in a buffer containing 0.5M NaCl. Among the hybridizing phage was one that could be distinguished from GDF-8-containing phage on the basis of its reduced hybridization intensity to the GDF-8 probe. Partial nucleotide sequence analysis of the genomic insert present in this weakly hybridizing phage showed that this clone contained a sequence highly related to but distinct from murine GDF-8.

A partial nucleotide sequence of the genomic insert present in this phage is shown in FIG. 1a. The sequence contained an open reading frame extending from nucleotides 198 to 575 that showed significant homology to the known members of the TGF-β superfamily (see below). Preceding this sequence was a 3' splice consensus sequence at precisely the same position as in the GDF-8 gene. This new TGF-β family member was given the designation GDF-11 (growth/differentiation factor-11).

EXAMPLE 2

Expression of GDF-11

Figure 2B:
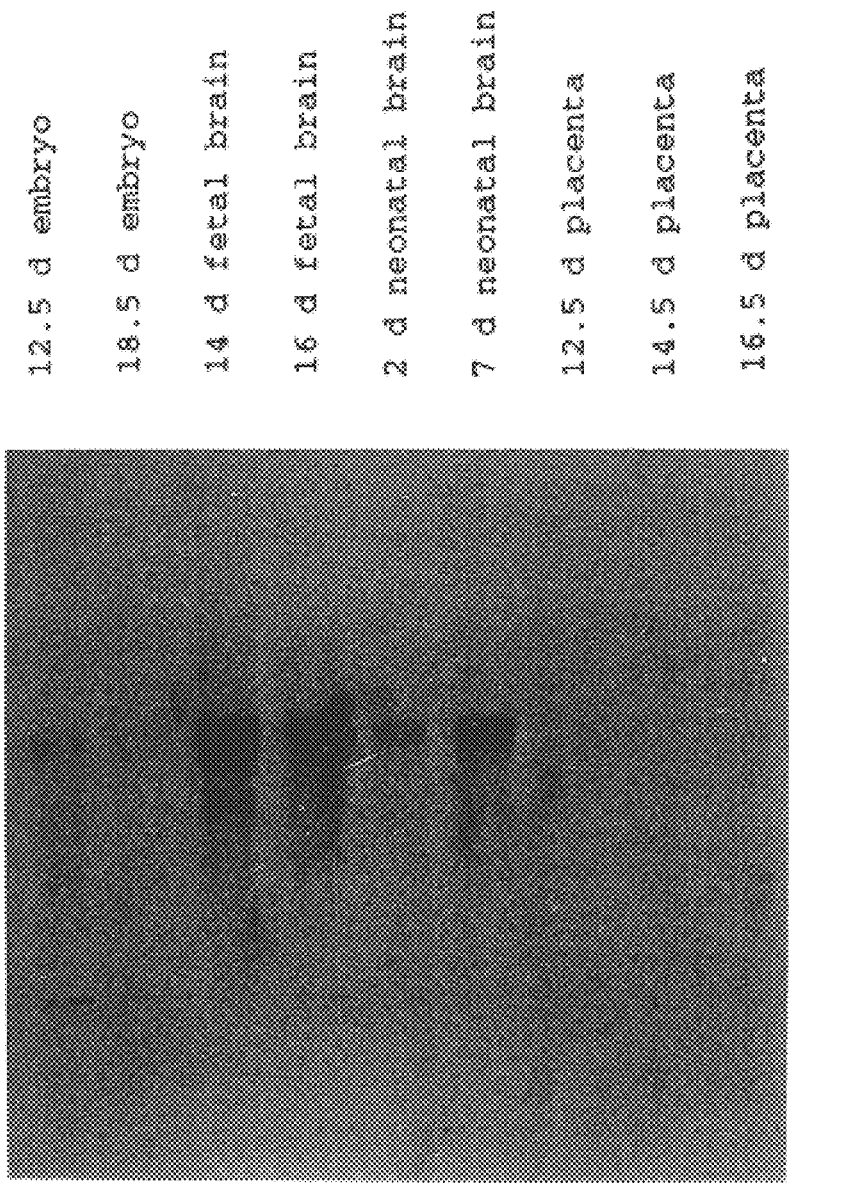

To determine the expression pattern of GDF-11, RNA samples prepared from a variety of tissues were screened by Northern analysis. RNA isolation and Northern analysis were carried out as described previously (Lee, Mol. Endocrinol., 4:1034, 1990) except that the hybridization was carried out in 5X SSPE, 10% dextran sulfate, 50% formamide, 1% SDS, 200 $\mu$g/ml salmon DNA, and 0.1% each of bovine serum albumin, ficoll, and polyvinylpyrrolidone. Five micrograms of twice poly A-selected RNA prepared from each tissue (except for 2 day neonatal brain, for which only 3.3 $\mu$g RNA were used) were electrophoresed on formaldehyde gels, blotted, and probed with GDF-11. As shown in FIG. 2, the GDF-11 probe detected two RNA species, approximately 4.2 and 3.2 kb in length, in adult thymus, brain, spleen, uterus, and muscle as well as in whole embryos isolated at day 12.5 or 18.5 and in brain samples taken at various stages of development. On longer exposures of these blots, lower levels of GDF-11 RNA could also be detected in a number of other tissues.

EXAMPLE 3

Isolation of cDNA Clones Eecoding GDF-11

In order to isolate cDNA clones encoding GDF-11, a cDNA library was prepared in the lambda ZAP II vector (Stratagene) using RNA prepared from human adult spleen. From 5 $\mu$g of twice poly A-selected RNA prepared from human spleen, a cDNA library consisting of 21 million recombinant phage was constructed according to the instructions provided by Stratagene. The library was screened without amplification. Library screening and characterization of CDNA inserts were carried out as described previously (Lee, Mol. Endocrinol., 4:1034, 1990). From this library, 23 hybridizing phage were obtained.

The entire nucleotide sequence of the clone extending furthest toward the 5' end of the gene was determined. The 1258 base pair sequence contained a single long open reading frame beginning from the 5' end of the clone and extending to a TAA stop codon. Because the open reading frame and the homology with GDF-8 (see below) extended to the very 5' end of the clone, it seemed likely that this clone was missing the coding sequence corresponding to the N-terminal portion of the GDF-11 precursor protein. In order to obtain the remaining portion of the GDF-11 sequence, several genomic clones were isolated by screening a human genomic library with the human GDF-11 cDNA probe. Partial sequence analysis of one of these genomic clones showed that this clone contained the GDF-11 gene. From this clone, the remaining GDF-11 coding sequence was obtained. FIG. 1b shows the predicted sequence of GDF-11 assembled from the genomic and CDNA sequences. Nucleotides 136 to 1393 represent the extent of the sequence obtained from a cDNA clone. Nucleotides 1 to 135 were obtained from a genomic clone. The sequence has been arbitrarily numbered beginning with a Sac II site present in the genomic clone, but the location of the mRNA start site is not known. The sequence contains a putative initiating methionine at nucleotide 54. Whether the sequence upstream of this methionine codon is all present in the MRNA is not known. Beginning with this methionine codon, the open reading frame extends for 407 amino acids. The sequence contains one potential N-linked glycosylation site at asparagine 94. The sequence contains a predicted RXXR proteolytic cleavage site at amino acids 295 to 298, and cleavage of the precursor at this site would generate an active C-terminal fragment 109 amino acids in length with a predicted molecular weight of approximately 12,500 kD. In this region, the predicted murine and human GDF-11 amino acid sequences are 100% identical. The high degree of sequence conservation across species suggests that GDF-11 plays an important role in vivo.

Figure 3:
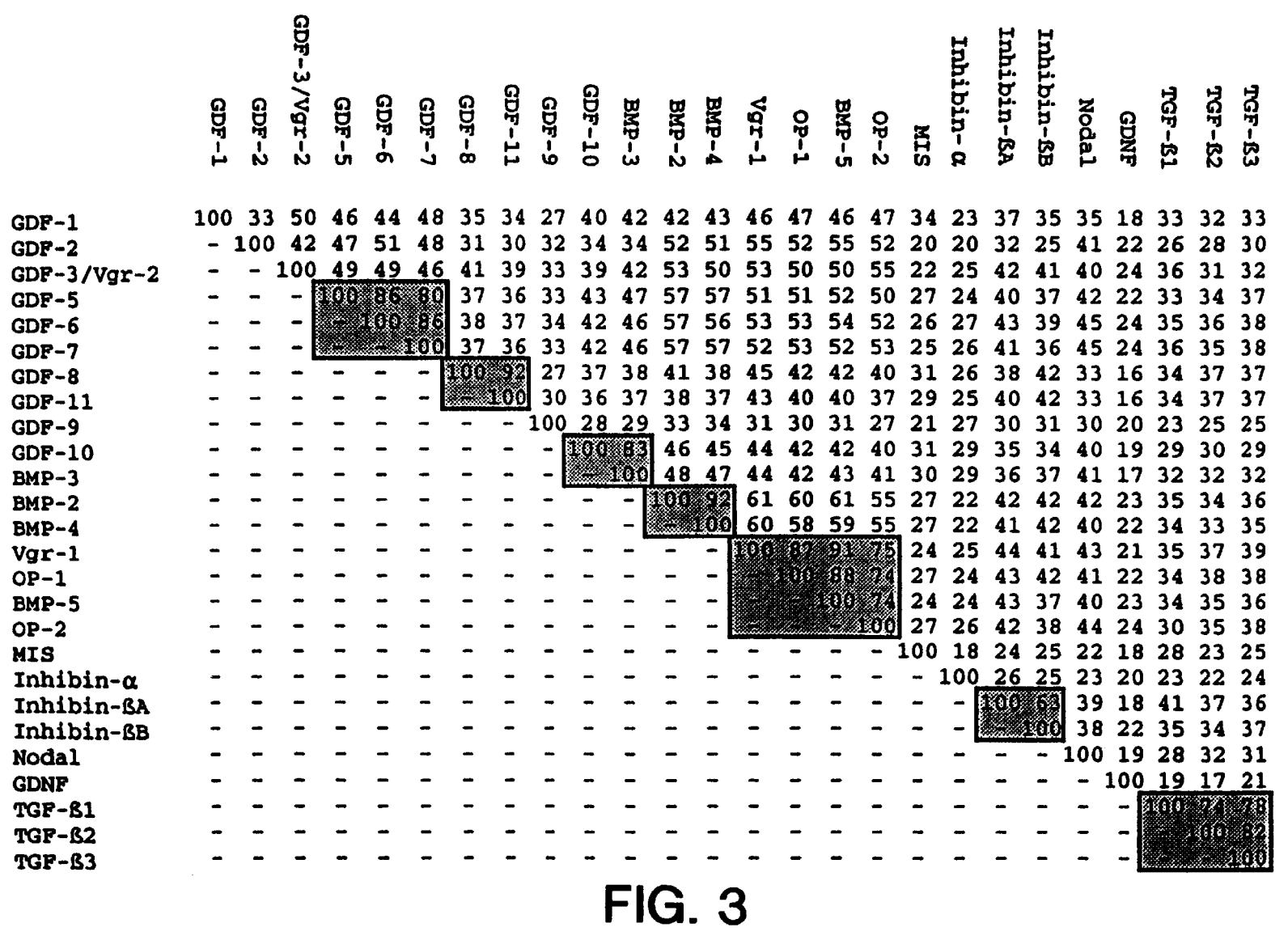

The C-terminal region following the predicted cleavage site contains all the hallmarks present in other TGF-β family members. GDF-11 contains most of the residues that are highly conserved in other family members, including the seven cysteine residues with their characteristic spacing. Like the TGF-β's, the inhibin β's, and GDF-8, GDF-11 also contains two additional cysteine residues. In the case of TGF-β2, these additional cysteine residues are known to form an intramolecular disulfide bond (Daopin, et al., Science, 257:369, 1992; Schlunegger and Grutter, Nature, 358:430, 1992). A tabulation of the amino acid sequence homologies between GDF-11 and the other TGF-β family members is shown in FIG. 3. Numbers represent percent amino acid identities between each pair calculated from the first conserved cysteine to the C-terminus. Boxes represent homologies among highly-related members within particular subgroups. In this region, GDF-11 is most highly related to GDF-8 (92% sequence identity).

An alignment of GDF-8 (SEQ ID NO:5) and GDF-11 (SEQ ID NO:6) amino acid sequences is shown in FIG. 4. The two sequences contain potential N-linked glycosylation signals (NIS) and putative proteolytic processing sites (RSRR) at analogous positions. The two sequences are related not only in the C-terminal region following the putative cleavage site (90% amino acid sequence identity), but also in the pro-region of the molecules (45% amino acid sequence identity).

EXAMPLE 4

Construction of a Hybrid GDF-8/GDF11 Gene

Figure 5:
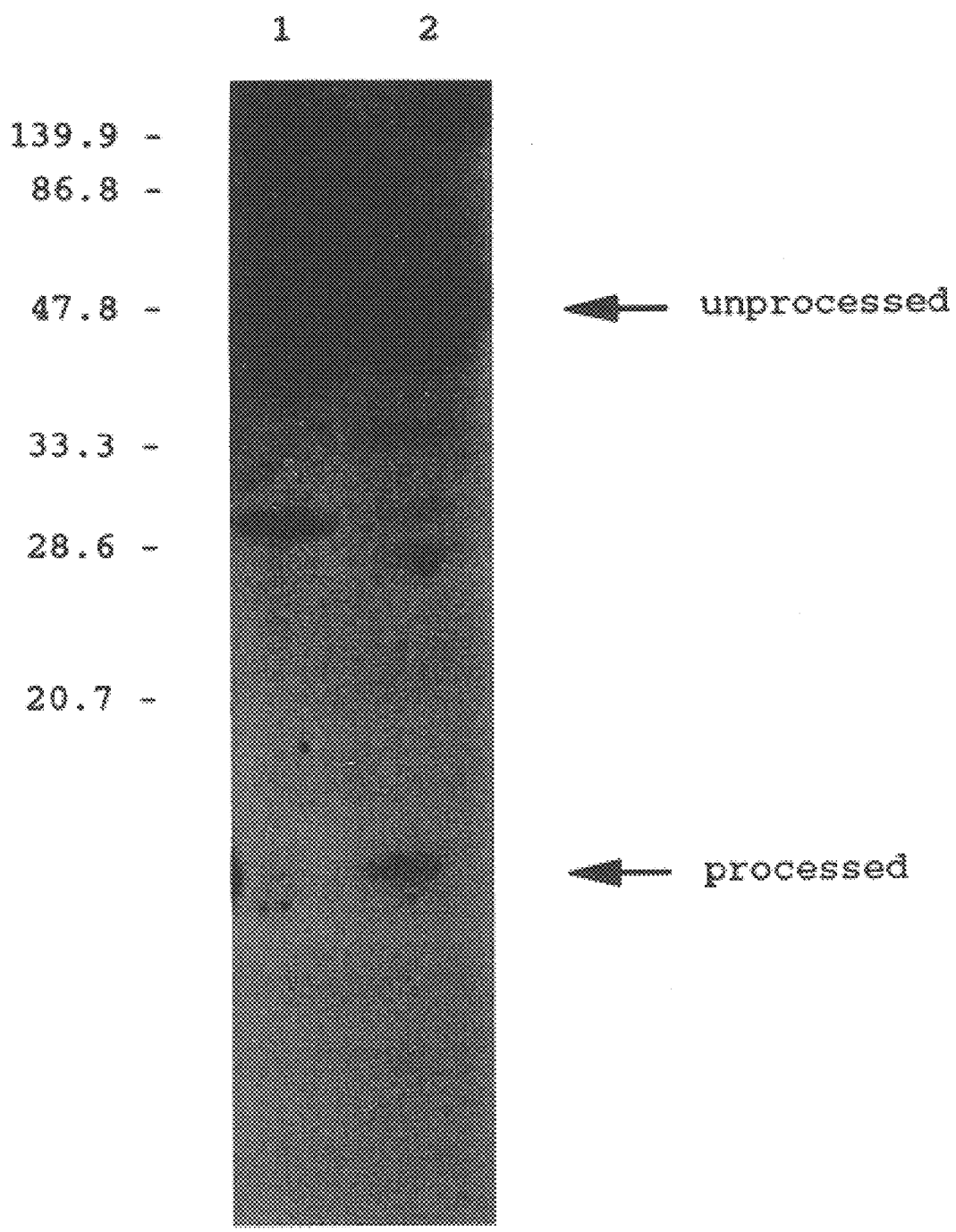
FIG. 5 shows the expression of GDF-11 in mammalian cells. Conditioned medium prepared from Chinese hamster ovary cells transfected with a hybrid GDF-8/GDF-11 gene (see text) cloned into the MSXND expression vector in either the antisense (lane 1) or sense (lane 2) orientation was dialyzed, lyophilized, and subjected to Western analysis using antibodies directed against the C-terminal portion of GDF-8 protein. Arrows at right indicate the putative unprocessed (pro-GDF-8/GDF-11) or processed GDF-11 proteins. Numbers at left indicate mobilities of molecular weight standards.

In order to express GDF-11 protein, a hybrid gene was constructed in which the N-terminal region of GDF-11 was replaced by the analogous region of GDF-8. Such hybrid constructs have been used to produce biologically-active BMP-4 (Hammonds, et al., Mol. Endocrinol., 5:149, 1991) and Vg-1 (Thomsen and Melton, Cell, 74:433, 1993). In order to ensure that the GDF-11 protein produced from the hybrid construct would represent authentic GDF-11, the hybrid gene was constructed in such a manner that the fusion of the two gene fragments would occur precisely at the predicted cleavage sites. In particular, an AvaII restriction site is present in both sequences at the location corresponding to the predicted proteolytic cleavage site. The N-terminal pro-region of GDF-8 up to this AvaII site was obtained by partial digestion of the clone with AvaII and fused to the C-terminal region of GDF-11 beginning at this AvaII site. The resulting hybrid construct was then inserted into the PMSXND mammalian expression vector (Lee and Nathans, J. Biol. Chem., 263:3521) and transfected into Chinese hamster ovary cells. As shown in FIG. 5, Western analysis of conditioned medium from G418-resistant cells using antibodies raised against the C-terminal portion of GDF-8 showed that these cells secreted GDF-11 protein into the medium and that at least some of the hybrid protein was proteolytically processed. Furthermore, these studies demonstrate that the antibodies directed against the C-terminal portion of GDF-8 will also react with GDF-11 protein.

EXAMPLE 5

Chromosomal Localization of GDF-11

In order to map the chromosomal location of GDF-11, DNA samples from human/rodent somatic cell hybrids (Drwinga, et al., Genomics, 16:311–313, 1993; Dubois and Naylor, Genomics, 16:315–319, 1993) were analyzed by polymerase chain reaction followed by Southern blotting. Polymerase chain reaction was carried out using primer #101, 5'-GAGTCCCGCTGCTGCCGATATCC-3', (SEQ ID NO:7) and primer #102, 5'-TAGAGCATGTTGATTGGGGACAT-3', (SEQ ID NO:8) for 35 cycles at 94° C. for 2 minutes, 58° C. for 1 minutes, and 72° C. for 1 minute. These primers correspond to nucleotides 981 to 1003 and the reverse complement of nucleotides 1182 to 1204, respectively, in the human GDF-11 sequence. PCR products were electrophoresed on agarose gels, blotted, and probed with oligonucleotide #104, 5'-AAATATCCGCATACCCATTT-3', (SEQ ID NO:9) which corresponds to a sequence internal to the region flanked by primer #101 and #102. Filters were hybridized in 6×SSC, 1×Denhardt's solution, 100 μg/ml yeast transfer RNA, and 0.05% sodium pyrophosphate at 50° C.

Figure 6:
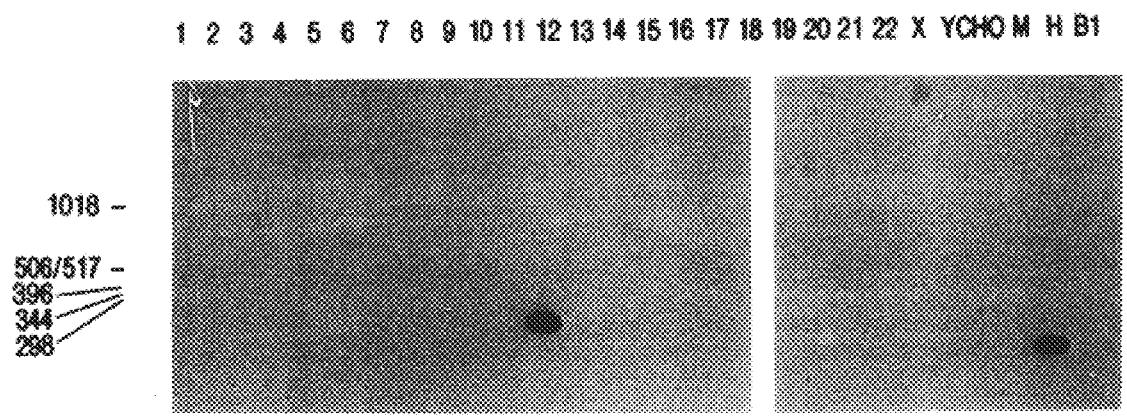
FIG. 6 shows the chromosomal mapping of human GDF-11. DNA samples prepared from human/rodent somatic cell lines were subjected to PCR, electrophoresed on agarose gels, blotted, and probed. The human chromosome contained in each of the hybrid cell lines is identified at the top of each of the first 24 lanes (1–22, X, and Y). In the lanes designated CHO, M, and H, the starting DNA template was total genomic DNA from hamster, mouse, and human sources, respectively. In the lane marked B1, no template DNA was used. Numbers at left indicate the mobilities of DNA standards.

As shown in FIG. 6, the human-specific probe detected a band of the predicted size (approximately 224 base pairs) in the positive control sample (total human genomic DNA) and in a single DNA sample from the human/rodent hybrid panel. This positive signal corresponds to human chromosome 12. The human chromosome contained in each of the hybrid cell lines is identified at the top of each of the first 24 lanes (1–22, X, and Y). In the lanes designated CHO, M, and H, the starting DNA template was total genomic DNA from hamster, mouse, and human sources, respectively. In the lane marked B1, no template DNA was used. Numbers at left indicate the mobilities of DNA standards. These data show that the human GDF-11 gene is located on chromosome 12.

Figure 7A:
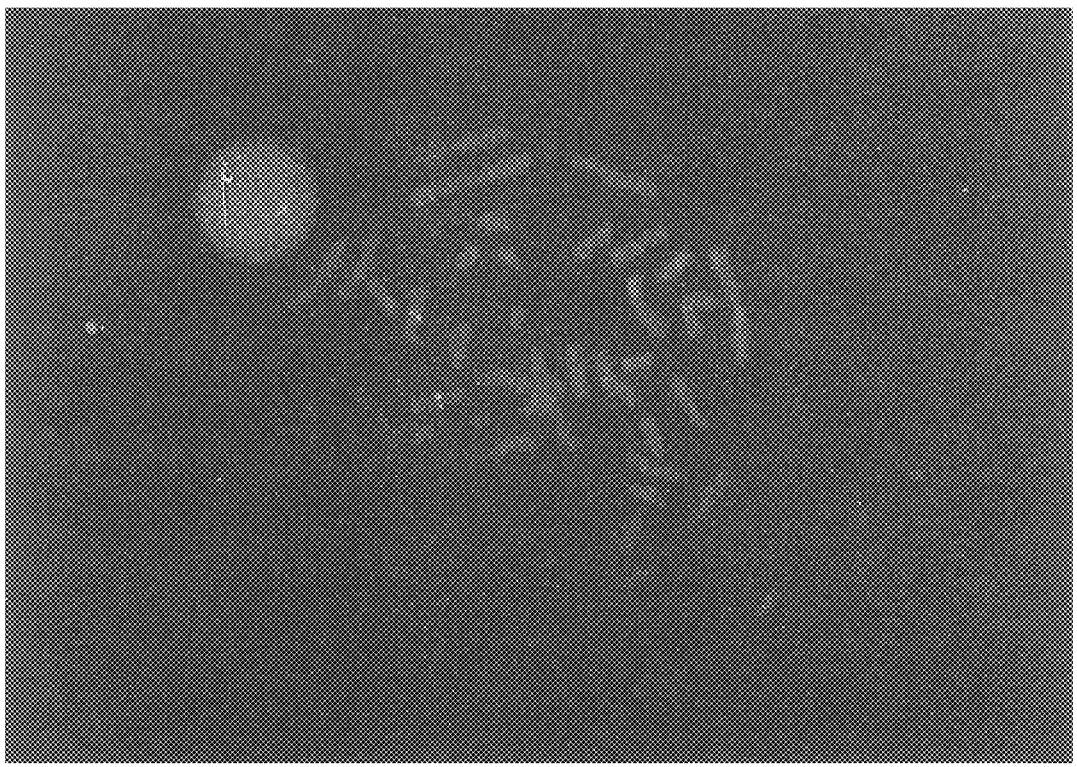
FIG. 7 shows the FISH localization of GDF-11. Metaphase chromosomes derived from peripheral blood lymphocytes were hybridized with digoxigenin-labelled human GDF-11 probe (a) or a mixture of human GDF-11 genomic and chromosome 12-specific centromere probes (b) and analyzed as described in the text. A schematic showing the location of GDF-11 at position 12q13 is shown in panel (c).
Figure 7B:
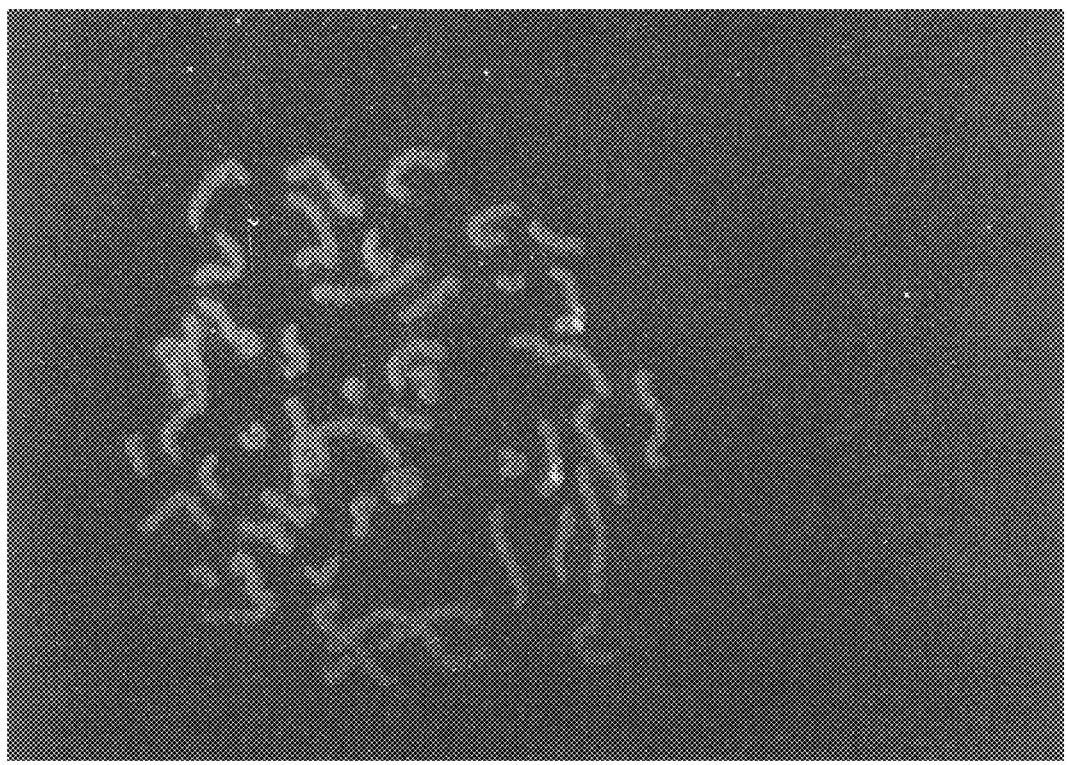
Figure 7C:
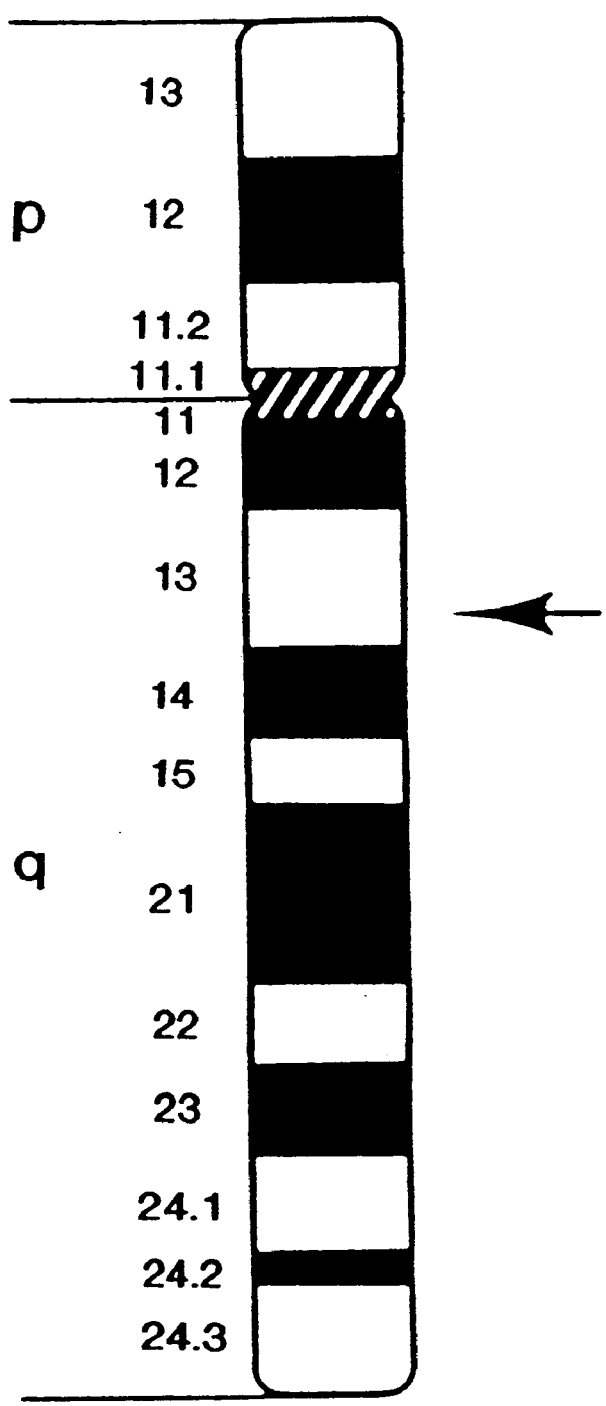

In order to determine the more precise location of GDF-11 on chromosome 12, the GDF-11 gene was localized by florescence in situ hybridization (FISH). These FISH localization studies were carried out by contract to BIOS laboratories (New Haven, Conn.). Purified DNA from a human GDF-11 genomic clone was labelled with digoxigenin dUTP by nick translation. Labelled probe was combined with sheared human DNA and hybridized to normal metaphase chromosomes derived from PHA stimulated peripheral blood lymphocytes in a solution containing 50% formamide, 10% dextran sulfate and 2×SSC. Specific hybridization signals were detected by incubating the hybridized slides in fluorescein-conjugated sheep antidigoxigenin antibodies. Slides were then counterstained with propidium iodide and analyzed. As shown in FIG. 7a, this experiment resulted in the specific labelling of the proximal long arm of a group C chromosome, the size and morphology of which were consistent with chromosome 12. In order to confirm the identity of the specifically labelled chromosome, a second experiment was conducted in which a chromosome 12-specific centromere probe was cohybridized with GDF-11. As shown in FIG. 7b, this experiment clearly demonstrated that GDF-11 is located at a position which is 23% of the distance from the centromere to the telomere of the long arm of chromosome 12, an area which corresponds to band 12q13 (FIG. 7c). A total of 85 metaphase cells were analyzed and 80 exhibited specific labelling.

EXAMPLE 6

GDF-11 Transgenic Knockout Mice

Figure 9:
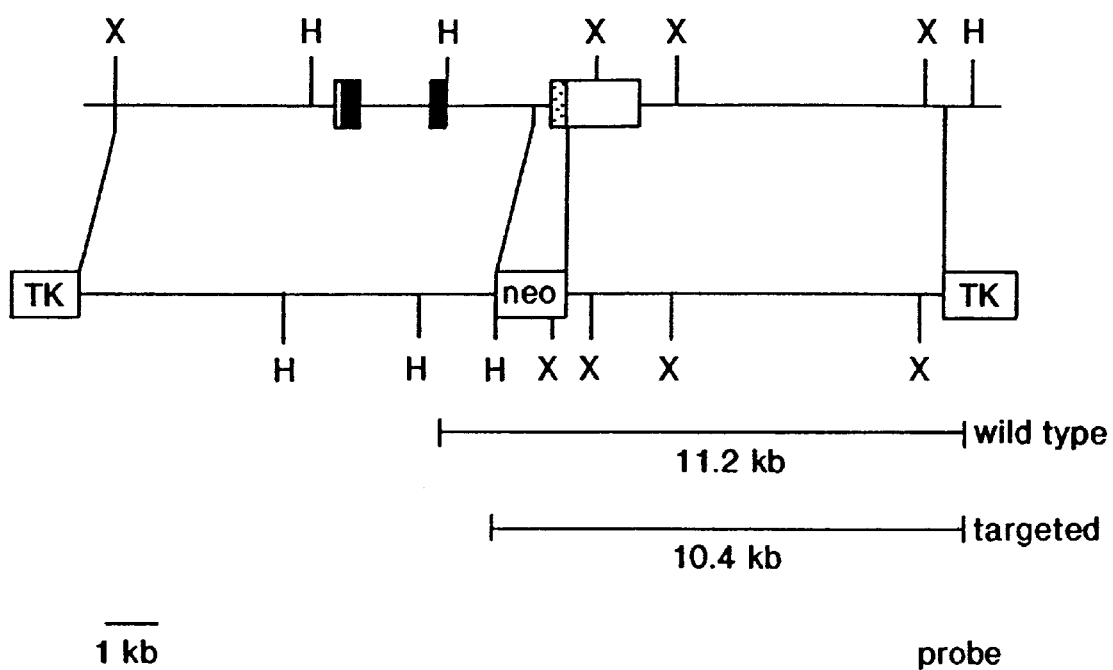
FIG. 9 shows a map of the GDF-8 locus (top line) and targeting construct (second line). The black and stippled boxes represent coding sequences for the pro- and C-terminal regions, respectively. The white boxes represent 5' and 3' untranslated sequences. A probe derived from the region downstream of the 3' homology fragment and upstream of the most distal HindIII site shown hybridizes to an 11.2 kb HindIII fragment in the GDF-8 gene and a 10.4 kb fragment in an homologously targeted gene. Abbreviations: H, HindIII; X, Xba I.

The GDF-11 gene is disrupted by homologous targeting in embryonic stem cells. To ensure that the resulting mice are null for GDF-11 function, the entire mature C-terminal region is deleted and replaced by a neo cassette (example using GDF-8 sequences is shown in FIG. 9). A murine 129 SV/J genomic library is prepared in lambda FIX II according to the instructions provided by Stratagene (La Jolla, Calif.). The structure of the GDF-11 gene was deduced from restriction mapping and partial sequencing of phage clones isolated from this library. Vectors for preparing the targeting construct were kindly provided by Philip Soriano and Kirk Thomas University. R1 ES cells are transfected with the targeting construct, selected with gancyclovir (2 $\mu$M) and G418 (250 $\mu$g/ml), and analyzed by Southern analysis. Homologously targeted clones are injected into C57BL/6 blastocysts and transferred into pseudopregnant females. Germline transmission of the targeted allele is obtained in male chimeras from independently-derived ES clones. Genomic Southern blots are hybridized at 42° C. as described above and washed in 0.2×SSC, 0.1% SDS at 42° C.

For whole leg analysis, legs of 14 week old mice are skinned, treated with 0.2 M EDTA in PBS at 4° C. for 4 weeks followed by 0.5 M sucrose in PBS at 4° C. For fiber number and size analysis, samples are directly mounted and frozen in isopentane as described (Brumback and Leech, *Color Atlas of Muscle Histochemistry*, pp. 9–33, PSG Publishing Company, Littleton, Ma., 1984). Ten to 30 $\mu$m sections are prepared using a cryostat and stained with hematoxylin and eosin. Muscle fiber numbers are determined from sections taken from the widest part of the tibialis cranialis muscle. Muscle fiber sizes are measured from photographs of sections of tibialis cranialis and gastrocnemius muscles. Fiber type analysis is carried out using the mysosin ATPase assay after pretreatment at pH 4.35 as described (Cumming, et al., *Color Atlas of Muscle Pathology*, pp. 184–185, 1994) and by immunohistochemistry using an antibody directed against type I myosin (MY32, Sigma) and the Vectastain method (Vector Labs); in the immunohistochemical experiments, no staining is seen when the primary antibodies were left out. Carcasses are prepared from shaved mice by removing the all of the internal organs and associated fat and connective tissue. Fat content of carcasses from 4 month old males is determined as described (Leshner, et al., *Physiol. Behavior*, 9:281, 1972).

For protein and DNA analysis, tissue is homogenized in 150 mM NaCl, 100 mM EDTA. Protein concentrations are determined using the Biorad protein assay. DNA is isolated by adding SDS to 1%, treating with 1 mg/ml proteinase K overnight at 55° C., extracting 3 times with phenol and twice with chloroform, and precipitating with ammonium acetate and EtOH. DNA is digested with 2 mg/ml RNase for 1 hour at 37° C., and following proteinase K digestion and phenol and chloroform extractions, the DNA is precipitated twice with ammonium acetate and EtOH.

Homologous targeting of the GDF-11 gene is seen in gancyclovir/G418 doubly-resistant ES cell clones. Following injection of these targeted clones into blastocysts, chimeras are obtained from independently-derived ES clones that produce heterozygous pups when crossed to C57BL/6 females (FIG. 8b).

Homozygous mutants are viable and fertile when crossed to C57BL/6 mice and to each other. Homozygous mutant animals, however, are approximately 30% larger than their heterozygous and wild type littermates. The difference between mutant and wild type body weights is relatively constant irrespective of age and sex in adult animals. Adult mutants display an abnormal body shape, with pronounced shoulders and hips. When the skin is removed from animals that had been sacrificed, it is apparent that the muscles of the mutants were much larger than those of wild type animals. The increase in skeletal muscle mass is widespread throughout the body. Individual muscles isolated from homozygous mutant animals weighed approximately 2–3 times more than those isolated from wild type littermates. Although the magnitude of the weight increase appears to roughly correlate with the level of GDF-11 expression in the muscles examined. To determine whether the increased muscle mass could account for the entire difference in total body weights between wild type and mutant animals or whether many tissues were generally larger in the mutants, the total body weights are compared to carcass weights. The difference in carcass weights between wild type and mutant animals is comparable to the difference in total body weights. Moreover, because the fat content of mutant and wild type animals is similar, these data are consistent with all of the total body weight difference resulting from an increase in skeletal muscle mass.

To determine whether the increase in skeletal muscle mass resulted from hyperplasia or from hypertrophy, histologic analysis of several different muscle groups is performed. The mutant muscle appears grossly normal. No excess connective tissue or fat is seen nor are there any obvious signs of degeneration, such as widely varying fiber sizes or centrally-placed nuclei.

Finally, fiber type analysis of various muscles is carried out to determine whether the number of both type I (slow) and type II (fast) fibers is increased in the mutant animals.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 1393 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: HUMAN GDF-11

(ix) FEATURE:
       (A) NAME/KEY: CDS
       (B) LOCATION: 54..1274

(xi) SEQUENCE DESCRIPTION: SEQ ID NO:1:

```
CCGCGGGACT CCGGCGTCCC CGCCCCCAG TCCTCCCTCC CCTCCCCTCC AGC ATG           56
                                                         Met
                                                          1

GTG CTC GCG GCC CCG CTG CTG CTG GGC TTC CTG CTC CTC GCC CTG GAG        104
Val Leu Ala Ala Pro Leu Leu Leu Gly Phe Leu Leu Leu Ala Leu Glu
              5                  10                  15

CTG CGG CCC CGG GGG GAG GCG GCC GAG GGC CCC GCG GCG GCG GCG GCG        152
Leu Arg Pro Arg Gly Glu Ala Ala Glu Gly Pro Ala Ala Ala Ala Ala
         20                  25                  30

GCG GCG GCG GCG GCG GCA GCG GCG GGG GTC GGG GGG GAG CGC TCC AGC        200
Ala Ala Ala Ala Ala Ala Ala Ala Gly Val Gly Gly Glu Arg Ser Ser
     35                  40                  45

CGG CCA GCC CCG TCC GTG GCG CCC GAG CCG GAC GGC TGC CCC GTG TGC        248
Arg Pro Ala Pro Ser Val Ala Pro Glu Pro Asp Gly Cys Pro Val Cys
 50                  55                  60                  65

GTT TGG CGG CAG CAC AGC CGC GAG CTG CGC CTA GAG AGC ATC AAG TCG        296
Val Trp Arg Gln His Ser Arg Glu Leu Arg Leu Glu Ser Ile Lys Ser
                 70                  75                  80

CAG ATC TTG AGC AAA CTG CGG CTC AAG GAG GCG CCC AAC ATC AGC CGC        344
Gln Ile Leu Ser Lys Leu Arg Leu Lys Glu Ala Pro Asn Ile Ser Arg
             85                  90                  95

GAG GTG GTG AAG CAG CTG CTG CCC AAG GCG CCG CCG CTG CAG CAG ATC        392
Glu Val Val Lys Gln Leu Leu Pro Lys Ala Pro Pro Leu Gln Gln Ile
        100                 105                 110

CTG GAC CTA CAC GAC TTC CAG GGC GAC GCG CTG CAG CCC GAG GAC TTC        440
Leu Asp Leu His Asp Phe Gln Gly Asp Ala Leu Gln Pro Glu Asp Phe
115                 120                 125

CTG GAG GAG GAC GAG TAC CAC GCC ACC ACC GAG ACC GTC ATT AGC ATG        488
Leu Glu Glu Asp Glu Tyr His Ala Thr Thr Glu Thr Val Ile Ser Met
130                 135                 140                 145

GCC CAG GAG ACG GAC CCA GCA GTA CAG ACA GAT GGC AGC CCT CTC TGC        536
Ala Gln Glu Thr Asp Pro Ala Val Gln Thr Asp Gly Ser Pro Leu Cys
                150                 155                 160

TGC CAT TTT CAC TTC AGC CCC AAG GTG ATG TTC ACA AAG GTA CTG AAG        584
Cys His Phe His Phe Ser Pro Lys Val Met Phe Thr Lys Val Leu Lys
            165                 170                 175

GCC CAG CTG TGG GTG TAC CTA CGG CCT GTA CCC CGC CCA GCC ACA GTC        632
Ala Gln Leu Trp Val Tyr Leu Arg Pro Val Pro Arg Pro Ala Thr Val
        180                 185                 190
```

```
TAC CTG CAG ATC TTG CGA CTA AAA CCC CTA ACT GGG GAA GGG ACC GCA      680
Tyr Leu Gln Ile Leu Arg Leu Lys Pro Leu Thr Gly Glu Gly Thr Ala
        195                 200                 205

GGA GGG GGC GGA GGC CGG CGT CAC ATC CGT ATC CGC TCA CTG AAG          728
Gly Gly Gly Gly Gly Arg Arg His Ile Arg Ile Arg Ser Leu Lys
210                 215                 220                 225

ATT GAG CTG CAC TCA CGC TCA GGC CAT TGG CAG AGC ATC GAC TTC AAG      776
Ile Glu Leu His Ser Arg Ser Gly His Trp Gln Ser Ile Asp Phe Lys
            230                 235                 240

CAA GTG CTA CAC AGC TGG TTC CGC CAG CCA CAG AGC AAC TGG GGC ATC      824
Gln Val Leu His Ser Trp Phe Arg Gln Pro Gln Ser Asn Trp Gly Ile
                245                 250                 255

GAG ATC AAC GCC TTT GAT CCC AGT GGC ACA GAC CTG GCT GTC ACC TCC      872
Glu Ile Asn Ala Phe Asp Pro Ser Gly Thr Asp Leu Ala Val Thr Ser
            260                 265                 270

CTG GGG CCG GGA GCC GAG GGG CTG CAT CCA TTC ATG GAG CTT CGA GTC      920
Leu Gly Pro Gly Ala Glu Gly Leu His Pro Phe Met Glu Leu Arg Val
        275                 280                 285

CTA GAG AAC ACA AAA CGT TCC CGG CGG AAC CTG GGT CTG GAC TGC GAC      968
Leu Glu Asn Thr Lys Arg Ser Arg Arg Asn Leu Gly Leu Asp Cys Asp
290                 295                 300                 305

GAG CAC TCA AGC GAG TCC CGC TGC TGC CGA TAT CCC CTC ACA GTG GAC     1016
Glu His Ser Ser Glu Ser Arg Cys Cys Arg Tyr Pro Leu Thr Val Asp
                310                 315                 320

TTT GAG GCT TTC GGC TGG GAC TGG ATC ATC GCA CCT AAG CGC TAC AAG     1064
Phe Glu Ala Phe Gly Trp Asp Trp Ile Ile Ala Pro Lys Arg Tyr Lys
            325                 330                 335

GCC AAC TAC TGC TCC GGC CAG TGC GAG TAC ATG TTC ATG CAA AAA TAT     1112
Ala Asn Tyr Cys Ser Gly Gln Cys Glu Tyr Met Phe Met Gln Lys Tyr
        340                 345                 350

CCG CAT ACC CAT TTG GTG CAG CAG GCC AAT CCA AGA GGC TCT GCT GGG     1160
Pro His Thr His Leu Val Gln Gln Ala Asn Pro Arg Gly Ser Ala Gly
355                 360                 365

CCC TGT TGT ACC CCC ACC AAG ATG TCC CCA ATC AAC ATG CTC TAC TTC     1208
Pro Cys Cys Thr Pro Thr Lys Met Ser Pro Ile Asn Met Leu Tyr Phe
370                 375                 380                 385

AAT GAC AAG CAG CAG ATT ATC TAC GGC AAG ATC CCT GGC ATG GTG GTG     1256
Asn Asp Lys Gln Gln Ile Ile Tyr Gly Lys Ile Pro Gly Met Val Val
                390                 395                 400

GAT CGC TGT GGC TGC TCT TAAGTGGGTC ACTACAAGCT GCTGGAGCAA            1304
Asp Arg Cys Gly Cys Ser
                405

AGACTTGGTG GGTGGGTAAC TTAACCTCTT CACAGAGGAT AAAAAATGCT TGTGAGTATG   1364

ACAGAAGGGA ATAAACAGGC TTAAAGGGT                                     1393

(2) INFORMATION FOR SEQ ID NO:2:

(i) SEQUENCE CHARACTERISTICS:
         (A) LENGTH: 407 amino acids
         (B) TYPE: amino acid
         (D) TOPOLOGY: linear (ii) MOLECULE TYPE: protein (xi) SEQUENCE DESCRIPTION: SEQ ID NO:2:

Met Val Leu Ala Ala Pro Leu Leu Leu Gly Phe Leu Leu Leu Ala Leu
  1               5                  10                  15

Glu Leu Arg Pro Arg Gly Glu Ala Ala Glu Gly Pro Ala Ala Ala Ala
            20                  25                  30

Ala Ala Ala Ala Ala Ala Ala Ala Ala Gly Val Gly Gly Glu Arg Ser
```

```
                 35                  40                  45
Ser Arg Pro Ala Pro Ser Val Ala Pro Glu Pro Asp Gly Cys Pro Val
     50                  55                  60

Cys Val Trp Arg Gln His Ser Arg Glu Leu Arg Leu Glu Ser Ile Lys
 65                  70                  75                  80

Ser Gln Ile Leu Ser Lys Leu Arg Leu Lys Glu Ala Pro Asn Ile Ser
                 85                  90                  95

Arg Glu Val Val Lys Gln Leu Leu Pro Lys Ala Pro Pro Leu Gln Gln
                100                 105                 110

Ile Leu Asp Leu His Asp Phe Gln Gly Asp Ala Leu Gln Pro Glu Asp
                115                 120                 125

Phe Leu Glu Glu Asp Glu Tyr His Ala Thr Thr Glu Thr Val Ile Ser
                130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
                180                 185                 190

Val Tyr Leu Gln Ile Leu Arg Leu Lys Pro Leu Thr Gly Glu Gly Thr
                195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
                290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

(2) INFORMATION FOR SEQ ID NO:3:

(i) SEQUENCE CHARACTERISTICS:
        (A) LENGTH: 630 base pairs
        (B) TYPE: nucleic acid
        (C) STRANDEDNESS: single
        (D) TOPOLOGY: linear
```

```
    (ii) MOLECULE TYPE: DNA (genomic)

(vii) IMMEDIATE SOURCE:
           (B) CLONE: MOUSE GDF-11

(ix) FEATURE:
           (A) NAME/KEY: CDS
           (B) LOCATION: 198..575

(xi) SEQUENCE DESCRIPTION: SEQ ID NO:3:

TCTAGATGTC AAGAGAAGTG GTCACAATGT CTGGGTGGGA GCCGTAAACA AGCCAAGAGG        60

TTATGGTTTC TGGTCTGATG CTCCTGTTGA GATCAGGAAA TGTTCAGGAA ATCCCCTGTT       120

GAGATGTAGG AAAGTAAGAG GTAAGAGACA TTGTTGAGGG TCATGTCACA TCTCTTTCCC       180

CTCTCCCTGA CCCTCAG CAT CCT TTC ATG GAG CTT CGA GTC CTA GAG AAC         230
                   His Pro Phe Met Glu Leu Arg Val Leu Glu Asn
                     1               5                  10

ACG AAA AGG TCC CGG CGG AAC CTA GGC CTG GAC TGC GAT GAA CAC TCG         278
Thr Lys Arg Ser Arg Arg Asn Leu Gly Leu Asp Cys Asp Glu His Ser
            15                  20                  25

AGT GAG TCC CGC TGC TGC CGA TAT CCT CTC ACA GTG GAC TTT GAG GCT         326
Ser Glu Ser Arg Cys Cys Arg Tyr Pro Leu Thr Val Asp Phe Glu Ala
        30                  35                  40

TTT GGC TGG GAC TGG ATC ATC GCA CCT AAG CGC TAC AAG GCC AAC TAC         374
Phe Gly Trp Asp Trp Ile Ile Ala Pro Lys Arg Tyr Lys Ala Asn Tyr
    45                  50                  55

TGC TCC GGC CAG TGC GAA TAC ATG TTC ATG CAA AAG TAT CCA CAC ACC         422
Cys Ser Gly Gln Cys Glu Tyr Met Phe Met Gln Lys Tyr Pro His Thr
60                  65                  70                  75

CAC TTG GTG CAA CAG GCC AAC CCA AGA GGC TCT GCT GGG CCC TGC TGC         470
His Leu Val Gln Gln Ala Asn Pro Arg Gly Ser Ala Gly Pro Cys Cys
                80                  85                  90

ACC CCT ACC AAG ATG TCC CCA ATC AAC ATG CTC TAC TTC AAT GAC AAG         518
Thr Pro Thr Lys Met Ser Pro Ile Asn Met Leu Tyr Phe Asn Asp Lys
            95                 100                 105

CAG CAG ATT ATC TAC GGC AAG ATC CCT GGC ATG GTG GTG GAT CGA TGT         566
Gln Gln Ile Ile Tyr Gly Lys Ile Pro Gly Met Val Val Asp Arg Cys
        110                 115                 120

GGC TGC TCC TAAGTTGTGG GCTACAGTGG ATGCCTCCCT CAGACCCTAC                 615
Gly Cys Ser
    125

CCCAAGAACC CCAGC                                                        630

(2) INFORMATION FOR SEQ ID NO:4:

(i) SEQUENCE CHARACTERISTICS:
           (A) LENGTH: 126 amino acids
           (B) TYPE: amino acid
           (D) TOPOLOGY: linear (ii) MOLECULE TYPE: protein (xi) SEQUENCE DESCRIPTION: SEQ ID NO:4:

His Pro Phe Met Glu Leu Arg Val Leu Glu Asn Thr Lys Arg Ser Arg
  1               5                  10                  15

Arg Asn Leu Gly Leu Asp Cys Asp Glu His Ser Ser Glu Ser Arg Cys
            20                  25                  30

Cys Arg Tyr Pro Leu Thr Val Asp Phe Glu Ala Phe Gly Trp Asp Trp
        35                  40                  45

Ile Ile Ala Pro Lys Arg Tyr Lys Ala Asn Tyr Cys Ser Gly Gln Cys
    50                  55                  60
```

```
Glu Tyr Met Phe Met Gln Lys Tyr Pro His Thr His Leu Val Gln Gln
 65                  70                  75                  80

Ala Asn Pro Arg Gly Ser Ala Gly Pro Cys Cys Thr Pro Thr Lys Met
                 85                  90                  95

Ser Pro Ile Asn Met Leu Tyr Phe Asn Asp Lys Gln Gln Ile Ile Tyr
            100                 105                 110

Gly Lys Ile Pro Gly Met Val Val Asp Arg Cys Gly Cys Ser
        115                 120                 125
```

(2) INFORMATION FOR SEQ ID NO:5:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-8

(ix) FEATURE:
        (A) NAME/KEY: Protein
        (B) LOCATION: 1..375

(xi) SEQUENCE DESCRIPTION: SEQ ID NO:5:

```
Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
 50                  55                  60

Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
```

```
                     245                 250                 255
Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
            290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

(2) INFORMATION FOR SEQ ID NO:6:

(i) SEQUENCE CHARACTERISTICS:
        (A) LENGTH: 407 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: GDF-11

(ix) FEATURE:
        (A) NAME/KEY: Protein
        (B) LOCATION: 1..407

(xi) SEQUENCE DESCRIPTION: SEQ ID NO:6:

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
            35                  40                  45

Ser Arg Pro Ala Pro Ser Val Ala Pro Glu Pro Asp Gly Cys Pro Val
50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
            130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175
```

```
Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
        290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..23

(xi) SEQUENCE DESCRIPTION: SEQ ID NO:7:

GAGTCCCGCT GCTGCCGATA TCC                                                 23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..23
```

-continued (xi) SEQUENCE DESCRIPTION: SEQ ID NO:8:

TAGAGCATGT TGATTGGGGA CAT                                           23

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..20

(xi) SEQUENCE DESCRIPTION: SEQ ID NO:9:

AAATATCCGC ATACCCATTT                                               20

Although the invention has been described with reference to the presently preferred embodiment, it should be understood that various modifications can be made without departing from the spirit of the invention. Accordingly, the invention is limited only by the following claims.

What is claimed is:

1. A method for increasing the muscle mass in an animal comprising administering to the animal an antibody, or fragment thereof, which specifically binds to growth differentiation factor-11 (GDF-11) polypeptide having an amino acid sequence as set forth in SEQ ID NO: 6, wherein the antibody is administered in an amount that inhibits the growth regulating activity of GDF-11 on muscle cells, thereby increasing muscle mass in the animal.

2. The method of claim 1, wherein GDF-11 antibody is administered to a domesticated animal.

3. The method of claim 1, wherein the antibody is a monoclonal antibody or a polyclonal antibody.

4. The method of claim 1, wherein the antibody is administered by intravenous, intramuscular, multiple bolus, or subcutaneous injections.

5. The method of claim 4, wherein the antibody is administered within a dose range of 0.1 µg/kg to 100 mg/kg.

6. The method of claim 4, wherein the antibody is formulated in a formulation suitable for administration by injection into an animal.

7. A method for inhibiting the growth regulating actions of growth differentiation factor-11 (GDF-11) on fetal or adult muscle cells or progenitor cells comprising administering to a subject as a therapeutic agent a GDF-11 monoclonal antibody or fragment thereof, which specifically binds to a GDF-11 polypeptide having an amino acid sequence as set forth in SEQ ID NO: 6, wherein the antibody is administered in an amount that inhibits the growth regulating actions of GDF-11 on fetal or adult muscle cells or progenitor cells.

8. The method of claim 7, wherein the monoclonal antibody is a humanized monoclonal antibody or a chimeric monoclonal antibody or fragment thereof.

9. The method of claim 7, wherein the monoclonal antibody increases the development of skeletal muscle.

10. The method of claim 7, wherein the monoclonal antibody is administered to a patient suffering from a disorder selected from the group consisting of muscle wasting disease, neuromuscular disorder, muscle atrophy and aging.

11. The method of claim 7, wherein the monoclonal antibody is administered to a patient suffering from a disorder selected from the group consisting of muscular dystrophy, spinal cord injury, traumatic injury, congestive obstructive pulmonary disease (COPD), AIDS and cachexia.

12. The method of claim 7, wherein the monoclonal antibody is administered to a patient with muscle wasting disease or disorder by intravenous, intramuscular or subcutaneous injection.

13. The method of claim 7, wherein the monoclonal antibody is administered within a dose range between about 0.1/kg to about 100 mg/kg.

14. The method of claim 7, wherein the monoclonal antibody is formulated in a formulation suitable for administration to a patient.

15. A method for increasing the muscle mass in a subject comprising administering to the subject a growth differentiation factor-11 polypeptide having an amino acid sequence as set forth in SEQ ID NO: 6, or antigenic peptide thereof, wherein the polypeptide or peptide is administered in an amount that induces a humoral immune response, wherein said humoral response inhibits the growth regulating activity of GDF-11 on muscle cells in the subject, thereby increasing muscle mass in the subject.

* * * * *